United States Patent
Fabre et al.

(10) Patent No.: US 11,137,396 B2
(45) Date of Patent: Oct. 5, 2021

(54) IN VITRO ASSAYS FOR ASSESSING CELL AGING

(71) Applicant: METAFORA BIOSYSTEMS, Evry (FR)

(72) Inventors: Pauline Fabre, Paris (FR); Christelle Cousin, Le Plessis-Robinson (FR); Guangqi E, Paris (FR); Vincent Petit, Paris (FR); Luc D'Auriol, Neuilly-sur-Seine (FR)

(73) Assignee: METAFORA BIOSYSTEMS, Evry (FR)

( * ) Notice: Subject to any disclaimer, the term of this patent is extended or adjusted under 35 U.S.C. 154(b) by 91 days.

(21) Appl. No.: 15/321,774

(22) PCT Filed: Jul. 3, 2015

(86) PCT No.: PCT/EP2015/065256
§ 371 (c)(1),
(2) Date: Dec. 23, 2016

(87) PCT Pub. No.: WO2016/001431
PCT Pub. Date: Jan. 7, 2016

(65) Prior Publication Data
US 2017/0160277 A1 Jun. 8, 2017

(30) Foreign Application Priority Data

Jul. 3, 2014 (EP) .................................. 14175534

(51) Int. Cl.
| | |
|---|---|
| *G01N 33/566* | (2006.01) |
| *G01N 33/50* | (2006.01) |
| *C12Q 1/6876* | (2018.01) |
| *C12Q 1/02* | (2006.01) |
| *C12Q 1/34* | (2006.01) |

(52) U.S. Cl.
CPC .............. *G01N 33/566* (2013.01); *C12Q 1/02* (2013.01); *C12Q 1/34* (2013.01); *C12Q 1/6876* (2013.01); *G01N 33/5073* (2013.01); *C12Q 2600/136* (2013.01); *C12Q 2600/158* (2013.01); *G01N 2333/705* (2013.01); *G01N 2500/10* (2013.01); *G01N 2800/52* (2013.01); *G01N 2800/7042* (2013.01)

(58) Field of Classification Search
CPC ............. G01N 2800/52; G01N 33/566; G01N 2333/705; G01N 2500/10; C12Q 1/6876
See application file for complete search history.

(56) References Cited

U.S. PATENT DOCUMENTS 8,574,852 B2  11/2013  Lee et al.

FOREIGN PATENT DOCUMENTS

| EP | 2 404 500 A1 | 1/2012 |
| EP | 2 533 042 A1 | 12/2012 |
| EP | 2 533 045 A1 | 12/2012 |
| FR | 2946347 | 12/2010 |
| JP | 2011-050358 | 3/2011 |
| JP | 2012-514744 | 6/2012 |
| WO | 2010/079208 | 7/2010 |

OTHER PUBLICATIONS

Giovannini et al., norganic phosphate export by the retrovirus receptor XPR1 in metazoans. Cell Rep. 3(6): 1866-1873, Jun. 27, 2013.*
Edinger, A., "Controlling Cell Growth and Survival Through Regulated Nutrient Transporter Expression," Biochem J., Aug. 15, 2007, vol. 406, No. 1, pp. 1-12.
Edinger, A., "Growth Factors Regulate Cell Survival by Controlling Nutrient Transporter Expression," Biochemical Society Transactions, vol. 33, No. 1, Feb. 1, 2005, pp. 225-227.
Giovannini, D. et al., "Inorganic Phosphate Export by the Retrovirus Receptor XPR1 in Metazoans," Cell Reports 3, Jun. 27, 2013, pp. 1866-1873.
Jiang, T. et al., "Lipoic Acid Restores Age-Associated Impairment of Brain Energy Metabolism Through the Modulation of Akt/JNK Signaling and PGC1α Transcriptional Pathway," Aging Cell, vol. 12, No. 6, Jul. 29, 2013, pp. 1021-1031.
Li, J. et al., "Profiling of Nutrient Transporter Expression in Human Stem Cell-Derived Cardiomyocytes Exposed to Tyrosine Kinase Inhibitor Anticancer Drugs Using RBD Ligands," Journal of Biomolecular Screening, vol. 19, No. 8, May 8, 2014, pp. 1185-1192.
Petit, V. et al., "Optimization of Tumor Xenograft Dissociation for the Profiling of Cell Surface Markers and Nutrient Transporters," Laboratory Investigation, vol. 93, No. 5, Mar. 4, 2013, pp. 611-621.
Wilkinson, J.E. et al., "Rapamycin Slows Aging in Mice," Aging Cell, 2012, pp. 675-682.
International Search Report issued in Application No. PCT/EP2015/065256, dated Oct. 14, 2015.
European Search Report issued in Application No. 14 17 5534, dated Dec. 9, 2014.
Dos Santos et al., "The effect of age on glucose uptake and GLUT1 and GLUT4 expression in rat skeletal muscle," Cell Biochemistry & Function,. Apr. 2012;30(3):191-7.

* cited by examiner

*Primary Examiner* — Ruixiang Li
(74) *Attorney, Agent, or Firm* — Nixon & Vanderhye

(57) ABSTRACT

Disclosed is an in vitro method for assessing, evaluating, monitoring or predicting cell aging of a cell, wherein the method includes measuring the expression level of at least one cell surface nutrient transporter on the cell.

7 Claims, 7 Drawing Sheets

Specification includes a Sequence Listing.

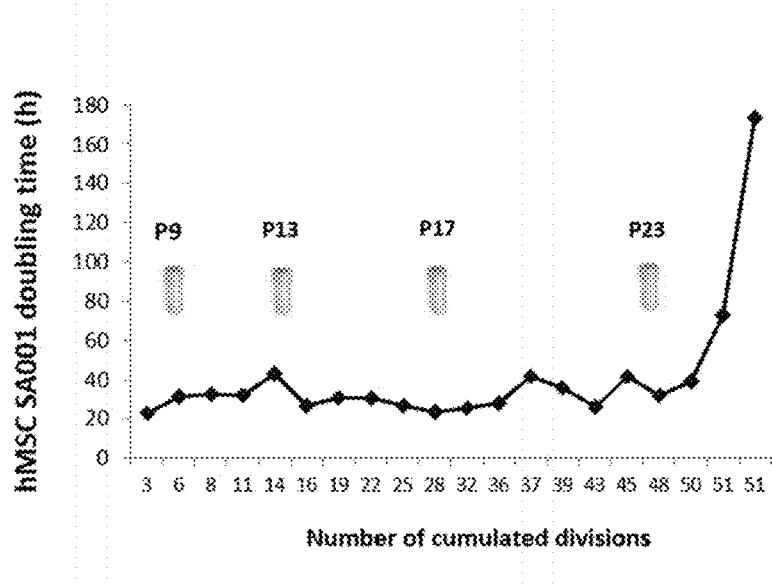
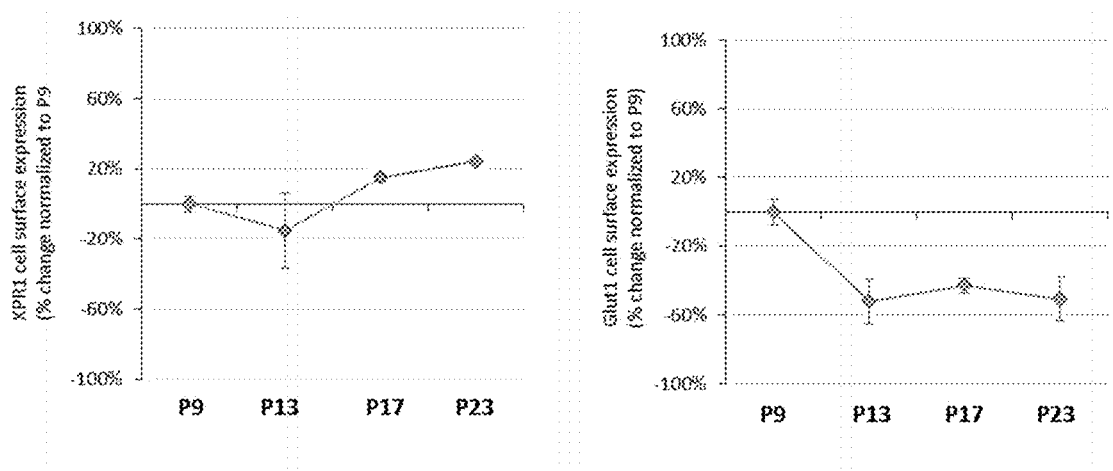
FIG. 1A-B

C
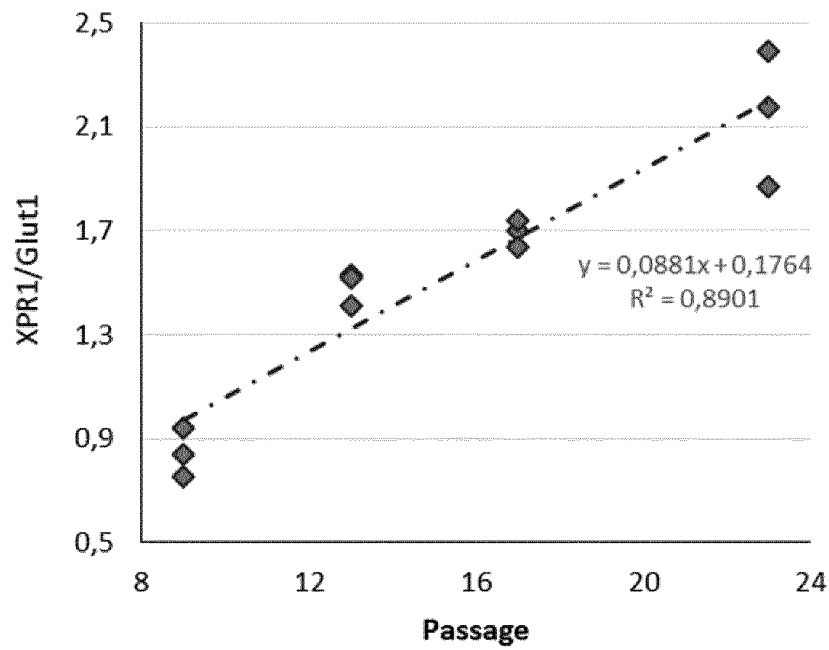
D
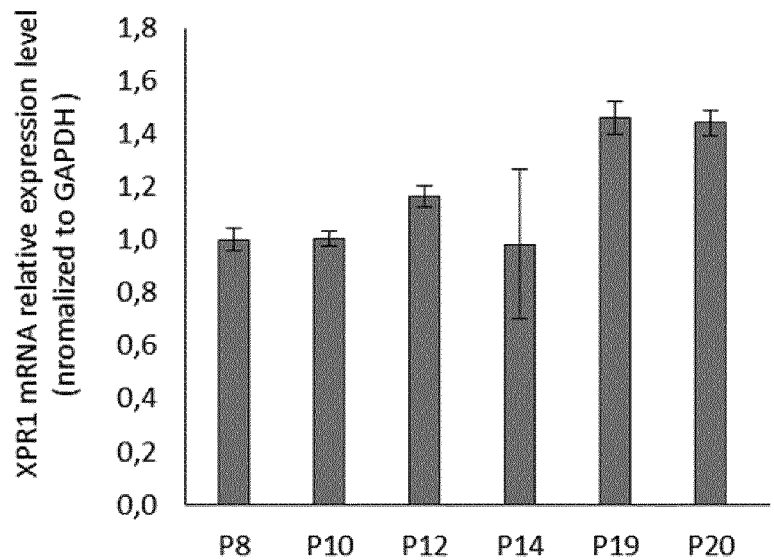
FIG. 1C-D

A
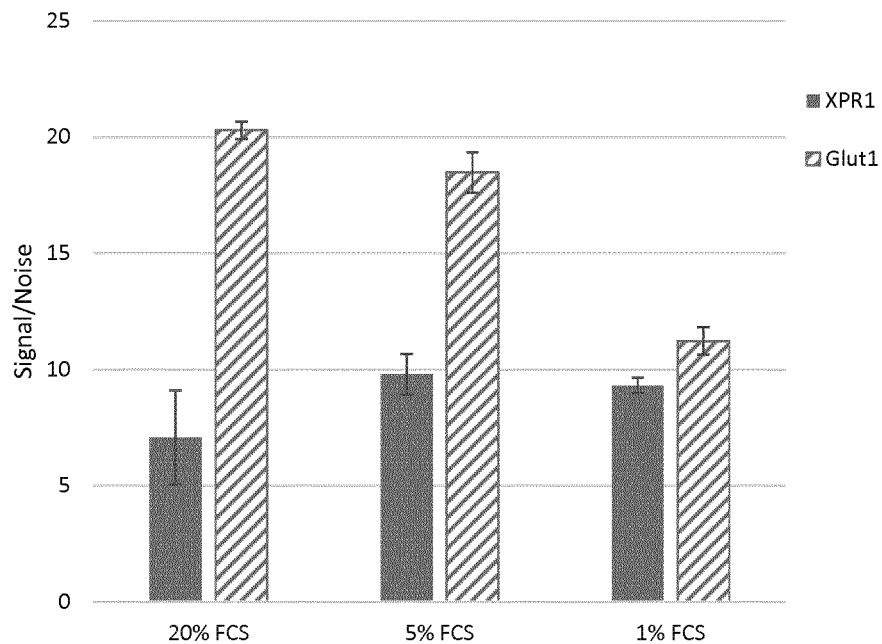
B
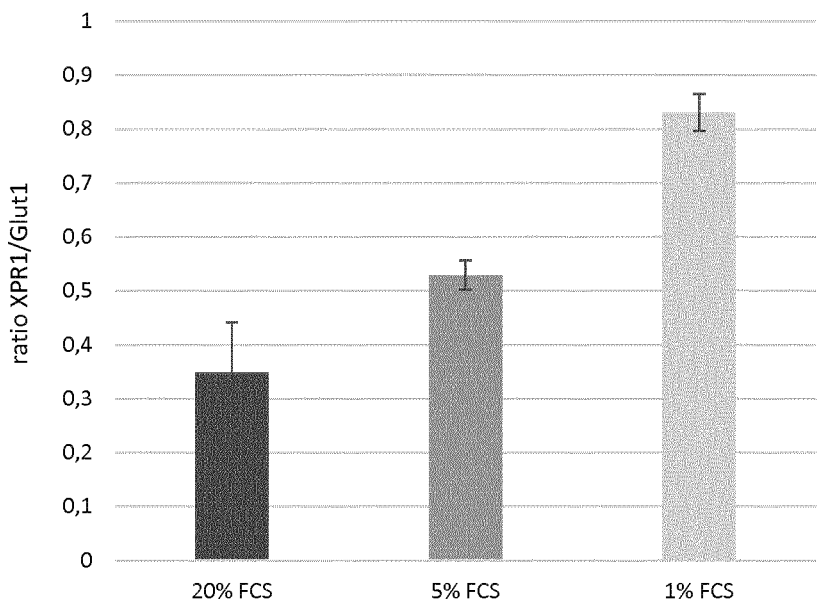
FIG. 4A-B

IN VITRO ASSAYS FOR ASSESSING CELL AGING

FIELD OF INVENTION

The present invention relates to methods for assessing cell aging and for screening compounds slowing down or accelerating cell aging (ie. anti-aging or pro-senescence drugs respectively). In particular, the present invention relates to a cell surface nutrient transporter, in particular XPR1, as a biomarker of cell aging.

BACKGROUND OF INVENTION

Regenerative medicine refers to the process of creating living, functional cells or tissues to repair and replace cells, tissue or organ function lost due to age, disease, damage or congenital defects. It may include replacing the damaged elements, but more usually corresponds to the administration of cells which will proliferate and/or differentiate in vivo in order to repair and/or replace the damaged tissue or organ. Regenerative medicine thus allows repair of previously irreparable tissues or organs, while overcoming the problem of the lack of organs available for transplantation.

Stem cells are defined by their self-renewal property (i.e. their ability to go through numerous cycles of cell division (mitosis) while maintaining an undifferentiated state) as well are their ability to generate differentiated cell types.

Stem cells may be classified according to their potency, i.e. their differentiation potential. Totipotent stem cells may differentiate into all cell types and thereby construct a complete viable organism. They result from the fusion of an egg and sperm cell. Cells resulting from the differentiation of totipotent cells are pluripotent cells: these may differentiate in any cell types of the three germ layers. Multipotent stem cells may differentiate into a limited number of cell types, generally of the progeny of the tissue of their location. Oligopotent stem cells may only differentiate into a few cell types, such as, for example, lymphoid or myeloid stem cells. Finally, unipotent stem cells may generate only their own cell type.

On the contrary to embryonic stem cells, adult stem cells are found in differentiated tissues throughout the body after development. Sources of adult stem cells include, for example, bone marrow, blood, cornea and retina, brain, skeletal muscle, dental pulp, liver, skin, gastrointestinal tract or pancreas.

Among stem cells, mesenchymal stem cells (MSC) are multipotent stem cells that can readily differentiate into lineages including osteoblasts, myocytes, chondrocytes and adipocytes. The clinical potential of adult MSC has been recently fully documented, and these cells are currently used in hundreds of clinical trials over the world. For therapy, two main sources of MSC may be used. First, cells may be autologous to the subject to be treated: cells are harvested from said subject, grown in specific culture condition to selectively induce differentiation and further re-administered to the subject. Second, allogenic MSC may be used, in order to reduce the time and cost linked to the preparation of cells to be administered to the subject. Therefore, banks of allogenic cells have to be built and amplified in culture for use in therapy.

However, even if adult stem cells present self-renewal ability and potency, these properties are not endless. Indeed, as culture passages accumulate, the doubling time of cells tends to increase, until reaching a non-dividing state, usually called senescence. Moreover, the differentiation potential of stem cells decreases with passages. In addition, significant decreased MSC expansion and differentiation potential were observed with increasing donor age.

There is thus a need for systems for assessing the proliferative capacity and differentiation potential of MSC, i.e. for assessing cell aging of cells. Such system may thus allow checking the therapeutic potential of cells before administration to patients.

The U.S. Pat. No. 8,574,852 describes a method for evaluating cell aging by measuring the expression level of cofilin. Cofilin is an intracellular protein that can bind to actin filaments and promote their dynamics for motility, development, polarity or cytokinesis.

Inventors demonstrated a correlation between expression level of cofilin in a target cell and the cellular age of said target cell.

Moreover, the European patent application EP 2 533 042 describes the detection of PW1 for monitoring cell aging.

However, the assays of the prior art for assessing cell aging usually involve detection of intracellular proteins, which are thus not directly detectable. Indeed, permeabilization of the cell is required, thus increasing the complexity of the detection method. There is thus a need for a marker of cell aging, which is expressed on cell surface and whose expression is dependent on the age of said cell.

Moreover, there is still a need for an early biomarker of cell aging, i.e. a biomarker whose expression, or change in expression, may be detected early in cell aging, in particular before the occurrence of any sign of senescence.

In the present invention, the Inventors demonstrated that the expression level of the XPR1 cell surface nutrient transporter correlates with cell aging. The present invention thus relates to the use of XPR1 as a biomarker (in particular as an early biomarker) of cell aging, and to the use of XPR1 in screening assays aiming at identifying compounds reversing, slowing-down or accelerating cell aging (ie. anti-aging or pro-senescence drugs respectively).

SUMMARY

The present invention thus relates to an in vitro method for assessing, evaluating, monitoring and/or predicting cell aging of a cell, wherein said method comprises measuring the expression level of at least one cell surface nutrient transporter on said cell. In one embodiment, the method of the invention further comprises comparing the measured expression level with a reference expression level.

In one embodiment, said at least one cell surface nutrient transporter is XPR1 and/or GLUT1, preferably XPR1.

In one embodiment, said cell is an animal cell, preferably a human or equine cell. In another embodiment, said cell is a stem cell, preferably an adult stem cell, more preferably a MSC, provided that said cell is not a human embryonic stem cell.

In one embodiment, said expression level is assessed at the RNA level, preferably by RT-PCR, RT-qPCR, Northern Blot and/or hybridization techniques. In another embodiment, said expression level is assessed at the protein level, preferably the measurement of the expression level of at least one cell surface nutrient transporter corresponds to the detection and quantification of said at least one cell surface nutrient transporter on the cell surface. In one embodiment, said detection and quantification of at least one cell surface nutrient transporter on the cell surface corresponds to detecting and/or quantifying binding of a ligand to a cell surface nutrient transporter, preferably said ligand is an antibody or is a receptor binding domain ligand (RBD) comprising a part or the totality of a receptor binding domain (RBD) derived from the soluble part of a glycoprotein of an enveloped virus. In one embodiment, said RBD is Xeno.RBD, and comprises or consists of the amino acid sequence SEQ ID NO: 1 or fragments thereof.

In one embodiment, said method is for assessing the quality of a batch of cells, preferably wherein said batch of cells is to be used in regenerative medicine or for in vitro screening assay.

The present invention also relates to the use of a cell surface nutrient transporter, preferably XPR1 and/or GLUT1, as a biomarker of cell aging or senescence, and/or as a biomarker of the accumulation of cell divisions, preferably as a biomarker of the proliferation capacity and/or of the differentiation capacity of a cell, or as a biomarker of stemness of a cell, or as a biomarker of the quality of a cell batch, in particular of a cell batch to be used in regenerative medicine or for in vitro screening assay.

Another object of the invention is a screening method for identifying compounds impacting cell aging, wherein said screening method comprises determining or measuring the expression level of at least one cell surface nutrient transporter. In one embodiment, said at least one cell surface nutrient transporter is XPR1 and/or GLUT1, preferably XPR1.

The present invention further relates to a kit for implementing the in vitro method of the invention or the screening method according of the invention, wherein said kit comprises means for determining or measuring the expression level of at least one cell surface nutrient transporter. In one embodiment, said means for determining or measuring the expression level of at least one cell surface nutrient transporter is a couple of PCR primer specific for said at least one cell surface nutrient transporter, an antibody specific for said at least one cell surface nutrient transporter and/or a RBD specific for said at least one cell surface nutrient transporter.

Definitions

In the present invention, the following terms have the following meanings:

- "Cell aging" refers to the progressive modification of the phenotype of a cell due to the successive cell divisions and/or to environmental conditions (such as, for example, culture medium composition, oxygen concentration and the like). In particular, as used herein, the term "cell aging" refers to the significant alteration of the phenotype of the cell, reflected by the loss of cell capacities. For MSC, in particular, cell aging may refer to the loss of the differentiation capacity (such as, for example, the progressive loss of the capacity to differentiate into the adipogenic, osteogenic, myogenic and/or chondrogenic lineage(s)), and/or to the loss of proliferation capacity (characterized ultimately by the complete incapacity of the cell to actively divide). In one embodiment, the term "cell aging" refers to the loss of the differentiation capacity of a MSC, i.e. a MSC overcoming cell aging has lost the capacity to differentiate into one (or at least one) lineage selected from the adipogenic, osteogenic, myogenic and chondrogenic lineage. In one embodiment, the MSC overcoming cell aging has lost the capacity to differentiate into two lineages selected from the adipogenic, osteogenic, myogenic and chondrogenic lineage. In another embodiment, the MSC overcoming cell aging has lost the capacity to differentiate into three lineages selected from the adipogenic, osteogenic, myogenic and chondrogenic lineage (preferably into the adipogenic, the osteogenic and the chondrogenic lineages). In another embodiment, the MSC overcoming cell aging has lost the capacity to differentiate into the adipogenic, osteogenic, myogenic and chondrogenic lineages. In one embodiment, cell aging results in senescence, and an "aged cell" is a cell entered in senescence, i.e. presenting signs of senescence (such as, for example, late signs of senescence listed thereafter). In one embodiment, the term "cell aging" refers to the loss of the proliferation capacity of a MSC, preferably, the number of cell division before the MSC enters in senescence is at most 20, more preferably is at most 15, 10, 9, 8, 7, 6, 5, 4, 3, 2, or 1 cell division(s).
- "Senescence" or "replicative senescence" as used herein refers to cellular senescence, wherein cellular senescence refers to a cellular state characterized by morphological changes (such as, for example, enlarged and irregular cell shapes) and ultimately a stop of proliferation. Senescence is a complex phenomenon, whose causes are probably multiple and still largely unknown. In particular, senescence may imply shortening of telomeres or modified telomere structure, as well as accumulation of DNA damages. Examples of late signs of senescence include, but are not limited to, increased doubling time; morphological changes that may be easily detected by microscopy (such as, for example, larger cells, larger nucleus, irregular shape, flat shape, granular cytoplasm and the like); loss of the potential to differentiate along the adipogenic, osteogenic, myogenic and/or chondrogenic lineages, increased expression of lysosomal β-galactosidase or of pH6 β-galactosidase (SA-β-gal); modification of the transcriptome of the cell, including, without limitation, up-regulation of the expression of at least one gene selected from the list comprising human glycoprotein NMB, regeneration-associated muscle protease homolog (RAMP), p53 apoptosis effector related to PMP-22 (PERP), lymphocytes antigen 96 (LY96), signal transducer and activator of transcription 1 (STAT1), prion protein (PRNP), cyclin-dependent kinase inhibitor 2A and plasminogen activator inhibitor type 1, or down-regulation of the expression of at least one gene selected from the list comprising hyaluronic acid synthetase 1 (HAS1), inhibitor of DNA binding 1 (ID1) and osteoprotegrin ligand (TNFSF11); or up-regulation of micro-RNA, such as, for example, micro-RNAs selected from the group comprising has-mir-371, has-mir-369-5P, has-mir-29c, has-mir-499 and has-let-7f.
- "Stemness" is a term referring to the common properties of stem cells, such as, for example, their self-renewal property (i.e. their ability to go through numerous cycles of cell division (mitosis) while maintaining an undifferentiated state) as well are their ability to generate differentiated cell types.
- "Proliferation capacity" or "proliferation potential" (that may be used interchangeably): refers to the capacity of a cell to actively divide.
- "Differentiation capacity" or "differentiation potential" (that may be used interchangeably): refers to the capacity of a cell to differentiate in at least one lineage. In one embodiment, the cell is MSC and the differentiation capacity of potential refers to the capacity of said MSC to differentiate into at least one of the osteogenic, myogenic, chondrogenic or adipogenic lineages; to differentiate into the three following lineages: osteogenic, chondrogenic and adipogenic lineages; or to differentiate into all of these 4 lineages.

"XPR1": refers to a phosphate exporter expressed by metazoans, in particular by humans, used as receptor by xenotropic murine leukemia virus (MLV), polytropic MLV and xenotropic murine leukemia virus-related virus (XMRV) (Giovannini et al, Cell Reports 3, 1866-1873, 2013). In one embodiment, XPR1 is human XPR1 (accession number AAH41142, SEQ ID NO: 21) encoded by SEQ ID NO: 22 (accession number BC041142.1). In one embodiment XPR1 comprises or consists of an amino acid sequence presenting a sequence identity of at least 70% with SEQ ID NO: 21, preferably a sequence identity of at least 75, 80, 85, 90, 91, 92, 93, 94, 95, 96, 97, 98, 99% or more with SEQ ID NO: 21. In one embodiment XPR1 is encoded by a nucleotide sequence presenting a sequence identity of at least 70% with SEQ ID NO: 22, preferably a sequence identity of at least 75, 80, 85, 90, 91, 92, 93, 94, 95, 96, 97, 98, 99% or more with SEQ ID NO: 22. In one embodiment, XPR1 comprises or consists of a fragment of SEQ ID NO: 21, preferably a fragment of at least about 100 amino acids, more preferably of at least about 150, 200, 250, 300, 350, 400, 450, 500, 550 or 600 amino acids.

As used herein; the term "identity", when used in a relationship between the sequences of two or more polypeptides or of two or more DNA sequences, refers to the degree of sequence relatedness between polypeptides or DNA sequences (respectively), as determined by the number of matches between strings of two or more amino acid residues or of two or more nucleotides respectively. "Identity" measures the percent of identical matches between the smaller of two or more sequences with gap alignments (if any) addressed by a particular mathematical model or computer program (i.e., "algorithms"). Identity of related polypeptides or DNA sequences can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988). Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. \2, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

"GLUT1": refers to a glucose importer expressed by metazoans, in particular by humans, used as receptor by Human T Leukemia viruses (HTLV) in particular. In one embodiment, GLUT1 is human GLUT1 (accession number NP_006507.2, SEQ ID NO: 23) encoded by SEQ ID NO: 24 (accession number NM_006516.2). In one embodiment GLUT1 comprises or consists of an amino acid sequence presenting a sequence identity of at least 70% with SEQ ID NO: 23, preferably a sequence identity of at least 75, 80, 85, 90, 91, 92, 93, 94, 95, 96, 97, 98, 99% or more with SEQ ID NO: 23. In one embodiment GLUT1 is encoded by a nucleotide sequence presenting a sequence identity of at least 70% with SEQ ID NO: 24, preferably a sequence identity of at least 75, 80, 85, 90, 91, 92, 93, 94, 95, 96, 97, 98, 99% or more with SEQ ID NO: 24. In one embodiment, GLUT1 comprises or consists of a fragment of SEQ ID NO: 23, preferably a fragment of at least about 100 amino acids, more preferably of at least about 150, 200, 250, 300, 350, 400 or 450 amino acids.

"Ligand" refers to any substance that forms a complex with a cell surface nutrient transporter. Typical ligands include, but are not limited to, polypeptides and proteins. As used herein, a polypeptide refers to a linear polymer of amino acids (preferably at least 50 amino acids) linked together by peptide bonds. A protein specifically refers to a functional entity formed of one or more polypeptides, and optionally of non-polypeptides cofactors.

"About" preceding a figure means plus or less 10% of the value of said figure.

DETAILED DESCRIPTION

The present invention relates to a method, preferably an in vitro method for assessing, evaluating, monitoring and/or predicting cell aging of a cell, wherein said method comprises determining or measuring the expression level of at least one cell surface nutrient transporter on said cell.

In one embodiment, said method further comprises comparing the measured expression level with a reference expression level.

With time, the doubling time of cells tends to increase, and the differentiation potential tends to decrease. Moreover, significant decreased MSC expansion and differentiation potential have been observed with increasing donor age.

Consequently, in one embodiment, the method of the invention is for measuring, assessing or determining the proliferation potential of a cell. In a particular embodiment, the method of the invention is for determining the number of culture passages or of cell divisions before the occurrence of senescence, or before the occurrence of first signs of senescence, in particular before the absence of cell division, or before the occurrence of late signs of senescence.

Examples of late signs of senescence include, but are not limited to, absence of cell division or increased doubling time (for example an increase of at least about 20%, preferably of at least about 30, 40, or 50% of the doubling time of the cell); morphological changes that may be easily detected by microscopy (such as, for example, larger cells, larger nuclei, irregular shape, flat shape, granular cytoplasm and the like); increased levels of lysosomal beta-galactosidase (which may be measured, for example, using a senescence-associated beta-galactosidase staining kit, such as the one provided by Cell Signaling, USA); increased expression of lysosomal β-galactosidase or of pH6 β-galactosidase (SA-β-gal) which may be detected by methods known by the skilled artisan, such as, for example, RT-qPCR (detection of expression at the mRNA level) or Western Blot (detection of expression at the protein level); modification of the transcriptome of the cell that may be easily assessed (such as, for example, by RT-PCR), including, without limitation, up-regulation of the expression of at least one gene selected from the list comprising human glycoprotein NMB, regeneration-associated muscle protease homolog (RAMP), p53 apoptosis effector related to PMP-22 (PERP), lymphocytes antigen 96 (LY96), signal transducer and activator of transcription 1 (STAT1), prion protein (PRNP), cyclin-dependent kinase inhibitor 2A and plasminogen activator inhibitor type 1, or down-regulation of the expression of at least one gene selected from the list comprising hyaluronic acid synthetase 1 (HAS1), inhibitor of DNA binding 1 (ID1) and osteoprotegrin ligand (TNFSF11); up-regulation of micro-RNA that may be easily assessed (such as, for example, by RT-PCR), such as, for example, micro-RNAs selected from the group comprising has-mir-371, has-mir-369-5P, has-mir-29c, has-mir-499 and has-let-7f; and loss of the potential to differentiate into specific lineages, such as, for example, the adipogenic, osteogenic, myogenic and/or chondrogenic lineages.

Methods for assessing the potential of a MSC to differentiate along the adipogenic, osteogenic and/or chondrogenic lineages are well known of the skilled artisan.

A non-limiting example of a method for assessing the potential of a MSC to differentiate along the adipogenic pathway is the following: cells were plated at $2 \cdot 10^4$ cells/cm$^2$ and cultured in DMEM with 10% FCS, 0.5 mM isobutyl-methylxanthine (IBMX), 1 µM dexamethasone, 10 µM insulin, 200 µM indomethacine, and Oil Red-O staining was performed after 21 days and analyzed semi-quantitatively at $\lambda$595 nm using a plate reader.

A non-limiting example of a method for assessing the potential of a MSC to differentiate along the osteogenic pathway is the following: cells are plated at $2 \cdot 10^4$ cells/cm$^2$ and cultured for 3 weeks in DMEM with 10% FCS (Invitrogen), 10 mM β-glycerophosphate, $10^{-7}$ M dexamethasone, and 0.2 mM ascorbic acid and with medium changes every 3 to 4 days. After 21 days, cells are analyzed by Alcaline phosphatase von Kossa or Alizarin red staining. Alizarin red staining is semi-quantitatively analyzed at $\lambda$595 nm using a plate reader.

A non-limiting example of a method for assessing the potential of a MSC to differentiate along the chondrogenic pathway is the following: a pellet of $2 \cdot 2 \cdot 10^5$ cells is cultured in a differentiation medium (such as, for example, OriCell™ Mesenchymal Stem Cell Chondrogenic Differentiation Medium (Cyagen) or Mesenchymal Stem Cell Chondrogenic Differentiation Medium (Promocell)) for 3 weeks with subsequent assessment of acid mucopolysaccharides by 1% Alcian blue (Chroma, Kongen, Germany) for 10-30 minutes.

Moreover, in one embodiment, the method of the invention is for measuring, assessing or determining the differentiation potential of a cell. In a particular embodiment, the method of the invention is for determining the number of culture passages or of cell divisions that the cell may undergo before the disappearance of the differentiation potential of said cell. For example, the method of the invention may be for determining the number of culture passages or of cell divisions before the loss of the capacity to differentiate into one particular lineage (adipogenic, osteogenic, myogenic or chondrogenic lineages), into the three following lineages: adipogenic, osteogenic and chondrogenic lineages, or the complete loss of the capacity of differentiation of the cell (i.e. the loss of the capacity to differentiate into the adipogenic, osteogenic, myogenic and chondrogenic lineages).

In one embodiment, the cell is an animal cell, such as, for example, a mammal cell, such as a rodent cell, a feline cell, a canine cell, an equine cell or a primate cell, preferably a human cell.

In one embodiment, the cell is a stem cell, preferably an adult stem cell, or a derivative thereof. Examples of adult stem cells include, but are not limited to, hematopoietic stem cells, mammary stem cells, intestinal stem cells, mesenchymal stem cells (MSC), endothelial stem cells, neural stem cells, olfactory adult stem cells, neural crest stem cells, testicular stem cells and muscle stem cells. In one embodiment, adult stem cells originate from bone marrow, mammary gland, intestine (in particular from the crypts of Lieberkuhn), placenta, adipose tissue, lung, blood, Wharton's jelly from umbilical cord, teeth, brain (such as, for example, from the subventricular zone, dentate gyrus or neocortex), nose (as olfactory adult stem cells may efficiently be harvested from olfactory mucosa cells from the lining of the nose), hair follicles, gastrointestinal tract, sciatic nerve, cardiac outflow tract, spinal and sympathetic ganglia or testicles.

In one embodiment, the stem cell is a multipotent stem cell, such as, for example, a MSC or a derivative thereof, such as, for example, osteocytes, chondrocytes, myocytes (e.g. cardiomyocytes) or adipocytes. In one embodiment, the MSC originate from bone-marrow, umbilical cord blood, Wharton's jelly (such as, for example, Wharton's jelly found within the umbilical cord), placenta, lung, adipose tissue, adult muscle, corneal stroma, teeth (such as, for example, from dental pulp of deciduous baby tooth), amniotic fluid, peripheral blood or the like. In one embodiment, the cell is hESC-SA001 derived MSC. In another embodiment, the cell is human primary MSC isolated and/or derived from bone marrow. In another embodiment, the cell is equine MSC.

In another embodiment, the stem cell is a unipotent stem cell or a derivative thereof, such as, for example, a keratinocyte.

In one embodiment, the cell is derived from a pluripotent stem cell such as an embryonic stem cell or an iPSC, wherein iPSC stands for induced pluripotent stem cell. iPSC is a type of pluripotent stem cells that can be generated directly from adult cells either by exposure to certain chemicals (such as, for example, valproic acid, BIX-01294, DZNep, SB431412, PD0325901, thiazovivin and mixtures thereof) and/or through transfection or transduction (for example of the set of genes Oct4 (Pou5f1), Sox2, cMyc, and Klf4).

According to an embodiment, the cell is not a human embryonic stem cell, and/or the recovering of the cell does not require the destruction of a human embryo.

In one embodiment, the cell is not a neuronal cell. In another embodiment, the cell is not a glial cell.

In one embodiment, the cells are cells recovered from a patient having a progeroid syndrome, preferably progeria cells. Progeroid syndromes are a group of rare genetic disorders that resemble to premature aging, a definition that can apply to a broad range of diseases. Familial Alzheimer's disease and familial Parkinson's disease are two well-known accelerated-aging diseases that are more frequent in older individuals while progeria (also referred as Hutchinson-Gilford Progeria Syndrome (HGPS)) is a very rare progressive disorder of childhood. It is characterized by features of premature aging (progeria), failure to thrive usually beginning in the first year of life resulting in short stature and low weight, deterioration of the layer of fat beneath the skin (subcutaneous adipose tissue), and characteristic craniofacial abnormalities, including frontal bossing, underdeveloped jaw (micrognathia), unusually prominent eyes and/or a small, "beak-like" nose.

In one embodiment, the cells are cells in culture, preferably are cell lines and/or are derived from primary cells, i.e. cells isolated straight from the tissue. In one embodiment, the cell is recovered from a sample from an individual, obtained for example by biopsy. Preferably, the step of recovering a sample from an individual is not part of the method of the present invention.

According to an embodiment, the method of the invention is thus for assessing the quality of a cell line or of primary cells in culture, and may comprise assessing the proliferation potential and/or the differentiation potential of the cells at a specific time. According to this embodiment, the method of the invention may thus correspond to a quality control method, aiming at checking the quality of a cell bank or batch. Said method may be useful, for example, for checking the proliferation and differentiation potentials of stem cells to be used in regenerative therapy, or for checking the proliferation and differentiation potentials of cells to be used in in vitro screening assays.

As used herein, the term "cell surface nutrient transporter" refers to a nutrient transporter anchored in the plasma membrane of a cell. Mammalian cells take up necessary nutrients via "nutrient transporters" on the cell surface and expel catabolites and other components. Nutrients and metabolites or catabolites are, for example, carbohydrates, amino acids, inorganic phosphate, nucleosides, lipids, vitamins, heme, ions etc. Nutrient transporters may be divided based on passive or active mechanisms of function. Passive (or facilitated) transporters allow diffusion of solutes across membranes down their electrochemical gradient. Active transporters create solute gradients across membranes, utilizing diverse energy-coupling mechanisms, such as, for example, ATP synthesis or hydrolysis. In one embodiment, the cell surface nutrient transporter belongs to the SLC series, wherein SLC stands for Solute Linked Carriers.

Examples of cell surface nutrient transporters include, but are not limited to, transporters of glucose, such as, for example, glucose importers (such as, for example, GLUT1); transporters of inorganic phosphate, such as, for example, inorganic phosphate importers (such as, for example, PiT1 or PiT2) or inorganic phosphate exporters (such as, for example, XPR1); transporters of amino acids, such as, for example, transporters of neutral amino acids (such as, for example, neutral amino acids importers (such as, for example, ASCT1 or ASCT2)), or transporters of cationic amino acids (such as, for example, CAT1); transporters of heme (such as, for example, FLVCR1); transporters of inositol, such as, for example, transporters of myo-inositol (such as, for example, SMIT1); and transporters of riboflavin, such as, for example, importers of riboflavin (such as, for example, RFT1, RFT3, PAR1 or PAR2).

In one embodiment, the cell surface nutrient transporter is a transporter of inorganic phosphate, such as, for example, an inorganic phosphate exporter (such as, for example, XPR1) or a transporter of glucose, such as, for example, a glucose importer (such as, for example, GLUT1).

In one embodiment, the method of the invention comprises measuring the expression level of XPR1 and/or of GLUT1. Preferably, the method of the invention comprises measuring the expression level of XPR1. In one embodiment, the method of the invention comprises measuring the expression level of XPR1 and of GLUT1.

In another embodiment, the at least one cell surface nutrient transporter does not consists in GLUT1, GLUT3 and/or GLUT4. In another embodiment, the at least one cell surface nutrient transporter does not consists in (a) glucose transporters.

As used herein, the term "expression" may refer alternatively to the transcription of a cell surface nutrient transporter (i.e. expression of the RNA) or to the translation (i.e. expression of the protein) of a cell surface nutrient transporter, or to the presence of the cell surface nutrient transporter at the surface of the cell.

Methods for determining the expression level are well-known from the skilled artisan, and include, without limitation, determining the transcriptome (in an embodiment wherein expression relates to transcription of a nutrient transporter) or proteome (in an embodiment wherein expression relates to translation of a nutrient transporter) of a cell.

In one embodiment of the invention, the expression of the cell surface nutrient transporter is assessed at the RNA level. Methods for assessing the transcription level of a transporter are well known in the prior art. Examples of such methods include, but are not limited to, RT-PCR, RT-qPCR, Northern Blot, hybridization techniques such as, for example, use of microarrays, and combination thereof including but not limited to, hybridization of amplicons obtained by RT-PCR, sequencing such as, for example, next-generation DNA sequencing (NGS) or RNA-seq (also known as "Whole Transcriptome Shotgun Sequencing") and the like.

Examples of PCR or qPCR primers that may be used for assessing the expression of XPR1 include, but are not limited to, the following couple of primers: Forward primer: 5'-AGAGCTTGGGAGACAAAGCA-3' (SEQ ID NO: 25)—Reverse primer: 5'-GTGGACACAACATTCGCAAC-3' (SEQ ID NO: 26).

Examples of PCR or qPCR primers that may be used for assessing the expression of GLUT1 include, but are not limited to, the following couple of primers: Forward primer: 5'-TCACTGTGCTCCTGGTTCTG-3' (SEQ ID NO: 27)—Reverse primer: 5'-CCTCGGGTGTCTTGTCACTT-3' (SEQ ID NO: 28).

In one embodiment of the invention, the expression of the cell surface nutrient transporter is assessed at the protein level. Methods for determining a protein level in a sample are well-known in the art. Examples of such methods include, but are not limited to, immunohistochemistry, Multiplex methods (Luminex), western blot, enzyme-linked immunosorbent assay (ELISA), sandwich ELISA, fluorescent-linked immunosorbent assay (FLISA), enzyme immunoassay (EIA), radioimmunoassay (RIA), flow cytometry (FACS) and the like.

In one embodiment of the invention, determining the expression level of a cell surface nutrient transporter specifically corresponds to the detection and quantification of said nutrient transporter present on the cell surface. Methods for analyzing the presence of a protein on the cell surface are well-known to the skilled artisan and include, without limitation, FACS analysis, immunohistochemistry, western blot associated with cell fractionation, enzyme-linked immunosorbent assay (ELISA), sandwich ELISA, fluorescent-linked immunosorbent assay (FLISA), enzyme immunoassay (EIA), radioimmunoassay (RIA) or image analysis, for example high content analysis and the like.

In one embodiment, determining the expression level of at least one cell surface nutrient transporter corresponds to detecting and/or quantifying binding of a ligand to a cell surface nutrient transporter. Preferably, said ligand is a receptor binding domain ligand and the method of the invention comprises detecting and/or quantifying a complex formed between said receptor binding domain ligand and a cell surface nutrient transporter. In another embodiment, said ligand is an antibody specific of said cell surface nutrient transporter, and the method of the invention comprises detecting and/or quantifying a complex formed between said antibody and said cell surface nutrient transporter.

The expression "detecting and/or quantifying binding of a ligand, such as, for example, a receptor binding domain ligand, to a cell surface nutrient transporter" means that when a cell surface nutrient transporter is present a complex is formed between the nutrient transporter and the ligand. That complex can be detected if the ligand has been for example, but not limited to, covalently coupled with a detectable molecule such as an antibody constant fragment (Fc) or a fluorescent compound (e.g. Cyanine dye, Alexa dye, Quantum dye, etc). The complex can also be detected if the ligand has been tagged with different means well known to the person skilled in the art. For example, but without limitation, a tag used in the invention can be a tag selected from the group comprising or consisting of Hemaglutinin Tag, Poly Arginine Tag, Poly Histidine Tag, Myc Tag, Strep Tag, S-Tag, HAT Tag, 3×Flag Tag, Calmodulin-binding peptide Tag, SBP Tag, Chitin binding domain Tag, GST Tag, Maltose-Binding protein Tag, Fluorescent Protein Tag, T7 Tag, V5 Tag and Xpress Tag. The use of the ligand therefore allows on the one hand the identification and detection of the cell surface nutrient transporter depending on the ligand used, and on the other hand the quantification of the complex formed.

In one embodiment, detecting or quantifying binding is conducted by flow cytometry, immunofluorescence or image analysis, for example high content analysis.

In a further aspect of the invention, the ligand is a receptor binding domain ligand, wherein said receptor binding domain ligand comprises a part or the totality of a receptor binding domain (RBD) derived from the soluble part of a glycoprotein of an enveloped virus that interacts with a cell surface nutrient transporter. Preferably, the ligand is soluble, i.e. it does not comprise a transmembrane domain, and is therefore not anchored to a membrane.

The expression "derived from the soluble part of the glycoprotein of an enveloped virus" means that the ligand is a fragment or a part of a glycoprotein contained in the envelope of a virus and can be obtained, for example, by cloning.

The term "glycoprotein" is to be understood as meaning an envelope glycoprotein, a coat glycoprotein or a fusion glycoprotein", wherein the term "glycoprotein" refers to a protein containing oligosaccharide chains covalently attached to polypeptide side-chains.

The expression "that interacts with a cell surface nutrient transporter" means that the glycoprotein is liable to recognize a receptor present on the surface of the cell. In one embodiment, a ligand that interacts with a cell surface nutrient transporter will thus form a complex with said cell surface nutrient transporter, which complex may be detected by a method as hereinabove described.

The receptor binding domain ligand containing part or the totality of the RBD can be fused to an antibody constant fragment (such as, for example, Fc fragment from rabbit or from mouse), and/or chemically modified to add a fluorochrome, or a fluorescent compound (e.g. Cyanine dye, Alexa dye, Quantum dye, etc).

RBDs are found, in particular, in glycoproteins of the envelope of viruses, therefore, the receptor binding domain ligand contains the total RBD or a fragment or part of the RBD.

In one embodiment, said virus is selected from the group comprising retroviruses, such as, for example, (i) gammaretroviruses such as for example, murine (MLV), feline (FeLV) or gibbon ape leukaemia virus (GaLV); and (ii) deltaretroviruses such as, for example, primate T cell leukaemia virus (such as, for example, human T cell leukaemia virus (HTLV) and simian T cell leukaemia virus (STLV)) or bovine leukaemia virus (BLV).

The gamma and deltaretroviruses encode an Env glycoprotein present in mature retrovirus virions. The Env protein is synthesized in the form of a propeptide, which is dived in Golgi apparatus by furine peptidase, resulting in two polypeptides: the transmembrane (TM) and the cell surface (SU) components. The SU domain contains two major subdomains: a domain of interaction with the TM domain and the RBD, the further being liable to interact with host cell membrane receptors.

In one embodiment, the soluble receptor binding domain ligand is isolated from the glycoprotein of Xenotropic Murine Leukaemia Virus, and is herein referred as Xeno.RBD.

In one embodiment, said Xeno.RBD comprises or consists of the amino acid sequence SEQ ID NO: 1 or fragments thereof.

In one embodiment, said fragment comprises or consists of amino acids 36 to 316 of SEQ ID NO: 1.

In one embodiment, said fragment comprises or consists of amino acids 1 to 297, 298, 299, 300, 301, 302, 303, 304, 305, 306, 307, 308, 309, 310, 311, 312, 313, 314 or 315 of SEQ ID NO: 1.

In another embodiment, said fragment comprises or consists of amino acids 36 to 297, 298, 299, 300, 301, 302, 303, 304, 305, 306, 307, 308, 309, 310, 311, 312, 313, 314 or 315 of SEQ ID NO: 1.

In another embodiment, said fragment comprises or consists of SEQ ID NO: 2, encoded by the DNA sequence SEQ ID NO: 3.

In another embodiment, said fragment comprises or consists of amino acids 36 to 296 of SEQ ID NO: 2.

In one embodiment, said Xeno.RBD comprises or consists of the amino acid sequence SEQ ID NO: 39 or fragments thereof.

In one embodiment, said fragment comprises or consists of amino acids 36 to 316 of SEQ ID NO: 39.

In one embodiment, said fragment comprises or consists of amino acids 1 to 297, 298, 299, 300, 301, 302, 303, 304, 305, 306, 307, 308, 309, 310, 311, 312, 313, 314 or 315 of SEQ ID NO: 39.

In another embodiment, said fragment comprises or consists of amino acids 36 to 297, 298, 299, 300, 301, 302, 303, 304, 305, 306, 307, 308, 309, 310, 311, 312, 313, 314 or 315 of SEQ ID NO: 39.

In another embodiment, said fragment comprises or consists of SEQ ID NO: 40, encoded by the DNA sequence SEQ ID NO: 41.

In another embodiment, said fragment comprises or consists of amino acids 36 to 296 of SEQ ID NO: 40.

In one embodiment, the soluble receptor binding domain ligand is isolated from the glycoprotein of Xenotropic MRV, and is herein referred as XMRV.RBD. In one embodiment, said XMRV.RBD comprises or consists of the amino acid sequence SEQ ID NO: 29 or fragments thereof.

In one embodiment, said fragment comprises or consists of amino acids 1 to 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282 or 283 of SEQ ID NO: 29.

In one embodiment, said fragment comprises or consists of amino acids 33 to 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282 or 283 of SEQ ID NO: 29.

In another embodiment, said fragment comprises or consists in SEQ ID NO: 35 (corresponding to amino acids 1 to 233 of SEQ ID NO: 29).

In another embodiment, said fragment comprises or consists in amino acids 33 to 233 of SEQ ID NO: 29.

In one embodiment, the soluble receptor binding domain ligand is isolated from the glycoprotein of Polytropic MLV, and is herein referred as PMLV.RBD.

In one embodiment, said PMLV.RBD comprises or consists of the amino acid sequence SEQ ID NO: 30 or fragments thereof.

In one embodiment, said fragment comprises or consists of amino acids 1 to 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278 or 279 of SEQ ID NO: 30.

In one embodiment, said fragment comprises or consists of amino acids 33 to 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278 or 279 of SEQ ID NO: 30.

In another embodiment, said fragment comprises or consists in SEQ ID NO: 36 (corresponding to amino acids 1 to 229 of SEQ ID NO: 30).

In another embodiment, said fragment comprises or consists of amino acids 33 to 229 of SEQ ID NO: 30.

In another embodiment, said PMLV.RBD comprises or consists of the amino acid sequence SEQ ID NO: 31 or fragments thereof.

In one embodiment, said fragment comprises or consists of amino acids 1 to 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269 or 270 of SEQ ID NO: 31.

In one embodiment, said fragment comprises or consists of amino acids 33 to 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269 or 270 of SEQ ID NO: 31.

In another embodiment, said fragment comprises or consists in SEQ ID NO: 37 (corresponding to amino acids 1 to 229 of SEQ ID NO: 31).

In another embodiment, said fragment comprises or consists of amino acids 33 to 229 of SEQ ID NO: 31.

In another embodiment, said PMLV.RBD comprises or consists of the amino acid sequence SEQ ID NO: 32 or fragments thereof.

In one embodiment, said fragment comprises or consists of amino acids 1 to 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278 or 279 of SEQ ID NO: 32.

In one embodiment, said fragment comprises or consists of amino acids 33 to 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278 or 279 of SEQ ID NO: 32.

In another embodiment, said fragment comprises or consists in SEQ ID NO: 38 (corresponding to amino acids 1 to 229 of SEQ ID NO: 32).

In another embodiment, said fragment comprises or consists of amino acids 33 to 229 of SEQ ID NO: 32.

In one embodiment, the soluble receptor binding domain ligand is isolated from the glycoprotein of Human T Leukaemia Virus-2, and is herein referred as HTLV2.RBD.

In one embodiment, said HTLV2.RBD comprises or consists of the amino acid sequence SEQ ID NO: 4 or fragments thereof.

In one embodiment, said fragment comprises or consists of amino acids 19 to 224 of SEQ ID NO: 4, or comprises or consists of amino acids 20 to 224 of SEQ ID NO: 4 or comprises or consists of amino acids 21 to 224 of SEQ ID NO: 4.

In one embodiment, said fragment comprises or consists of amino acids 1 to 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222 or 223 of SEQ ID NO: 4.

In another embodiment, said fragment comprises or consists of amino acids 19, 20 or 21 to 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222 or 223 of SEQ ID NO: 4.

In another embodiment, said fragment comprises or consists of SEQ ID NO: 5, encoded by the DNA sequence SEQ ID NO: 6.

In another embodiment, said fragment comprises or consists of amino acids 19, 20 or 21 to 178 of SEQ ID NO: 5.

In one embodiment, the soluble receptor binding domain ligand is isolated from the glycoprotein of Human T Leukaemia Virus-1, and is herein referred as HTLV1.RBD. In one embodiment, said HTLV1.RBD comprises or consists of the amino acid sequence SEQ ID NO: 7 or fragments thereof.

In one embodiment, said fragments comprise or consist of amino acids 1 to 183, 184, 185, 186, 187, 188, 189, 190, 191, 192, 193, 194, 195, 196, 197, 198, 199, 200, 201, 202, 203, 204, 205, 206, 207 or 208 of SEQ ID NO: 7.

In one embodiment, said fragments comprise or consist of amino acids 21 to 183, 184, 185, 186, 187, 188, 189, 190, 191, 192, 193, 194, 195, 196, 197, 198, 199, 200, 201, 202, 203, 204, 205, 206, 207 or 208 of SEQ ID NO: 7.

In another embodiment, said fragments comprise or consist in SEQ ID NO: 33 (corresponding to amino acids 1 to 182 of SEQ ID NO: 7).

In one embodiment, said fragments comprise or consist of amino acids 21 to 182 of SEQ ID NO: 7.

In one embodiment, the soluble receptor binding domain ligand is isolated from the glycoprotein of Human T Leukaemia Virus-4, and is herein referred as HTLV4.RBD. In one embodiment, said HTLV4.RBD comprises or consists of the amino acid sequence SEQ ID NO: 8 or fragments thereof.

In one embodiment, said fragments comprise or consist of amino acids 1 to 179, 180, 181, 182, 183, 184, 185, 186, 187, 188, 189, 190, 191, 192, 193, 194, 195, 196, 197, 198, 199, 200, 201, 202, 203 or 204 of SEQ ID NO: 8.

In one embodiment, said fragments comprise or consist of amino acids 21 to 179, 180, 181, 182, 183, 184, 185, 186, 187, 188, 189, 190, 191, 192, 193, 194, 195, 196, 197, 198, 199, 200, 201, 202, 203 or 204 of SEQ ID NO: 8.

In another embodiment, said fragments comprise or consist in SEQ ID NO: 34 (corresponding to amino acids 1 to 178 of SEQ ID NO: 8).

In another embodiment, said fragments comprise or consist in amino acids 21 to 178 of SEQ ID NO: 8.

In another embodiment, said HTLV4.RBD comprises or consists of the amino acid sequence SEQ ID NO: 42 or fragments thereof.

In one embodiment, said fragments comprise or consist of amino acids 1 to 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 710, 711, 712, 713, 714, 715, 716, 717, 718, 719, 720, 721, 722, 723, 724, 725, 726, 727, 728, 729, 730, 731, 732, 733, or 734 of SEQ ID NO: 42.

In one embodiment, said fragments comprise or consist of amino acids 24 to 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 710, 711, 712, 713, 714, 715, 716, 717, 718, 719, 720, 721, 722, 723, 724, 725, 726, 727, 728, 729, 730, 731, 732, 733, or 734 of SEQ ID NO: 42.

In another embodiment, said fragments comprise or consist of amino acids 22 to 237 of SEQ ID NO: 42, or comprise or consist of amino acids 23 to 237 of SEQ ID NO: 42, or comprise or consist of amino acids 24 to 237 of SEQ ID NO: 42.

In another embodiment, said fragments comprise or consist of amino acids 1 to 236 of SEQ ID NO: 42. In another embodiment, said fragments comprise or consist of amino acids 24 to 236 of SEQ ID NO: 42.

In another embodiment, said fragments comprise or consist of SEQ ID NO: 42, encoded by the DNA sequence SEQ ID NO: 45.

In one embodiment, the soluble receptor binding domain ligand is isolated from the glycoprotein of Human T Leukemia Virus-3, and is herein referred as HTLV3.RBD. In one embodiment, said HTLV3.RBD comprises or consists of the amino acid sequence SEQ ID NO: 43 or fragments thereof.

In one embodiment, said fragments comprises or consists of amino acids 1 to 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, or 492 of SEQ ID NO: 43 or fragments thereof.

In one embodiment, said fragments comprise or consist of amino acids 23 to 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, or 492 of SEQ ID NO: 43 or fragments thereof.

In another embodiment, said fragments comprise or consist of amino acids 1 to 180 of SEQ ID NO: 43. In another embodiment, said fragments comprise or consist of amino acids 23 to 180 of SEQ ID NO: 43.

In another embodiment, said fragments comprise or consist of SEQ ID NO: 43, encoded by the DNA sequence SEQ ID NO: 44.

According to a preferred embodiment, receptor binding domain ligands are selected from the group comprising the sequences SEQ ID NO: 1, 2, 4, 5, 7, 8, 29, 30, 31, 32, 33, 34, 35, 36, 37, 38, 39, 40, 42 and 43, fragments and variants thereof, more preferably selected from the group comprising the sequences SEQ ID NO: 2, 5, 33, 34, 35, 36, 37, 38 and 40, fragments and variants thereof. According to another embodiment, receptor binding domain ligands are encoded by a DNA sequence selected from the group comprising the sequences SEQ ID NO: 3, 6, 41, 44 and 45.

In one embodiment, the receptor binding domain ligand comprises or consists of a sequence presenting a sequence identity of at least 70% with one of the sequences SEQ ID NO: 1, 2, 4, 5, 7, 8, 29, 30, 31, 32, 33, 34, 35, 36, 37, 38, 39, 40, 42 and 43, preferably a sequence identity of at least about 75, 80, 85, 90, 91, 92, 93, 94, 95, 96, 97, 98, 99% or more with one of the sequences SEQ ID NO: 1, 2, 4, 5, 7, 8, 29, 30, 31, 32, 33, 34, 35, 36, 37, 38, 39, 40, 42 and 43.

In another embodiment, the receptor binding domain ligand is encoded by a DNA sequence presenting a sequence identity of at least 70% with one of the sequences SEQ ID NO: 3, 6, 41, 44 and 45, preferably a sequence identity of at least about 75, 80, 85, 90, 91, 92, 93, 94, 95, 96, 97, 98, 99% or more with one of the sequences SEQ ID NO: 3, 6, 41, 44 and 45.

In one embodiment, the receptor binding domain ligand is a variant of one of the polypeptide having the sequences SEQ ID NO: 1, 2, 4, 5, 7, 8, 29, 30, 31, 32, 33, 34, 35, 36, 37, 38, 39, 40, 42 and 43.

A polypeptide "variant" as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences and evaluating one or more biological activities of the polypeptide as described herein and/or using any of a number of techniques well known in the art. Modifications may be made in the structure of polypeptides and still obtain a functional molecule that encodes a variant or derivative polypeptide with desirable characteristics.

When it is desired to alter the amino acid sequence of a polypeptide to create an equivalent, or even an improved, variant or portion of a ligand of the invention, one skilled in the art will typically change one or more of the codons of the encoding DNA sequence. For example, certain amino acids may be substituted by other amino acids in a protein structure without appreciable loss of its ability to bind cell surface nutrient transporters. Since it is the binding capacity and nature of a protein that defines that protein's biological functional activity, certain amino acid sequence substitutions can be made in a protein sequence, and, of course, its underlying DNA coding sequence, and nevertheless obtain a protein with similar properties. It is thus contemplated that various changes may be made in the peptide sequences, or corresponding DNA sequences that encode said peptides without appreciable loss of their biological utility or activity. In many instances, a polypeptide variant will contain one or more conservative substitutions. A "conservative substitution" is one in which an amino acid is substituted by another amino acid that has similar properties, such that one skilled in the art of peptide chemistry would expect the secondary structure and hydropathic nature of the polypeptide to be substantially unchanged. As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine. Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of 1, 2, 3, 4, 5, 6, 7, 8, 9 or 10 amino acids. Variants may also (or alternatively) be modified by, for example, the deletion or addition of amino acids that have minimal influence on the immunogenicity, secondary structure and hydropathic nature of the polypeptide.

In one embodiment, the receptor binding domain ligand is a fusion protein comprising a part or the totality of a receptor binding domain fused to a detection tag, such as, for example, a Fc fragment or a GFP. Examples of Fc fragments include, but are not limited to, rabbit Fc fragment (amino acid sequence SEQ ID NO: 9, encoded by SEQ ID NO: 10), and mouse Fc fragment (amino acid sequence SEQ ID NO: 11, encoded by SEQ ID NO: 12).

In one embodiment, the receptor binding domain ligand is selected from the group comprising HTLV2.RBD fused to a mouse Fc fragment (encoded by the DNA sequence SEQ ID NO: 13), and Xeno.RBD fused to a rabbit Fc fragment (encoded by the DNA sequence SEQ ID NO: 14).

In one embodiment, the receptor binding domain ligand is obtained by a cloning method, such as, for example, using any production system known in the art, such as, for example, *E. coli*, yeast, baculovirus-insect cell, or mammalian cells such as HEK or CHO, expression system. In one embodiment, the sequence of the receptor binding domain ligand is fused in N-terminal to a peptide signal sequence allowing the secretion of said receptor binding domain ligand. Examples of peptide signal sequences include, but are not limited to, human IL-2 peptide signal (SEQ ID NO: 15), human albumin peptide signal (SEQ ID NO: 16), human chymotrypsinogen peptide signal (SEQ ID NO: 17), human trypsinogen-2 peptide signal (SEQ ID NO: 18), gaussia luciferase peptide signal (SEQ ID NO: 19), and mouse IgM peptide signal (SEQ ID NO: 20).

In one embodiment, the receptor binding domain ligand comprises a part or the totality of Xeno.RBD, XMRV.RBD or PMLV.RBD and binds to the XPR1 nutrient transporter. In one embodiment, the receptor binding domain ligand comprises a part or the totality of HTLV2.RBD, HTLV1.RBD, HTLV3.RBD or HTLV4.RBD and binds to the GLUT1 nutrient transporter.

As used herein, the term "reference" broadly encompasses any suitable reference expression level which may be used as a basis for comparison with respect to the measured expression level.

In one embodiment, the standard reference is a personalized reference, determined earlier in the same culture of cells as the one used for determining the expression level. In a first embodiment of the invention the reference expression level is the expression level measured in a culture of cells before, preferably 1, 2, 3, 4, 5, 6, 8, 9, 10 days or more before, or 1, 2, 3, 4, 5, 6, 7, 8 weeks before, or 1, 2, 3, 4, 5 months or more before, or 1, 2, 3, 4, 5 years or more before the day of performing the assay of the invention. In a second embodiment, the cells were frozen and subsequently thawed, and the reference expression level is the expression level measured before freezing.

According to these embodiments, a difference between the measured expression level and the personalized reference expression level is indicative of cell aging or of senescence.

In one embodiment of the invention, the reference expression level is the expression level measured in a "young" batch of cells. In one embodiment, a young batch of cells presents complete differentiation properties (such as, for example, in the case of MSC, young cells are able to differentiate along the osteogenic, chondrogenic and adipogenic lineages, and optionally into the myogenic lineage). In another embodiment, a young batch of cells presents complete proliferation capacities, with normal doubling time (normal doubling time depends on the type of cells). In another embodiment, a young batch of cells present no signs (in particular no late signs) of senescence (examples of late signs of senescence are listed hereinabove). In one embodiment, a young batch of cells may further divide at least 10 times, preferably at least 15, 20, 25, 30, 35, 40, 45, or 50 times before the occurrence of signs of senescence (in particular of last signs of senescence as listed in the present invention). In one embodiment, a young batch of cells has been passaged 10 times or less, preferably 9, 8, 7, 6, 5, 4, 3, 2, 1 time(s). According to this embodiment, a difference between the measured expression level and the reference expression level is indicative of cell aging or of senescence.

In one embodiment of the invention, the reference expression level is the expression level measured in an "old" batch of cells. In one embodiment, an old batch of cells presents significantly altered differentiation capacities, such as, for example, the cell is not capable anymore to differentiate into at least one specific cell lineage (such as, for example, in the case of MSC, differentiation in at least one of the osteogenic, chondrogenic, adipogenic or myogenic lineages is not possible anymore); or is not capable to differentiate into the three following lineages: osteogenic, chondrogenic and adipogenic lineages; or is not capable to differentiate anymore. In another embodiment, an old batch of cells is a batch of cells showing absence of cell division or increased doubling time (for example, double time increased by at least 20%, preferably at least 30, 40, or 50% as compared to the normal doubling time, which depends on the type of cells). In another embodiment, an old batch of cells is a batch of cells showing signs (in particular late signs) of senescence (for a list, see hereinabove). In another embodiment, an old batch of cells has been passaged 10 times or more, preferably 20, 25, 30, 35, 40, 45, 50 times or more. According to this embodiment, the absence of difference between the measured expression level and the reference expression level is indicative of cell aging or of senescence.

In one embodiment, the reference is constructed using algorithms and other methods of statistical and hierarchical classification.

In another aspect, the reference expression level is stored in a database to provide a stored expression level and the stored expression level is used to determine the difference in the expression level. The database may, for example, be stored on a computer or a server.

In one embodiment, the expression level is normalized, i.e. the expression level corresponds to a ratio between the expression of the cell surface nutrient transporter and the expression of another gene or protein.

In one embodiment, the cell surface nutrient transporter is XPR1 and the other gene or protein used for normalization is GLUT1. In another embodiment, the cell surface nutrient transporter is GLUT1 and the other gene or protein used for normalization is XPR1.

In another embodiment, the cell surface nutrient transporter is XPR1 or GLUT1, preferably is XPR1, and the other gene or protein used for normalization is selected from the group comprising GAPDH, CD29, CD44, CD73, CD105, and CD166.

In the present invention, two numeric values, in particular two expression levels, are considered as different if the first numeric value is higher (such as, for example, the first numeric value is about 20% higher than the second one, preferably is about 30, 40, 50, 60, 70, 80, 90% or more higher than the second one) or lower than the second one (such as, for example, the second numeric value is about 20% lower than the second one, preferably is about 30, 40, 50, 60, 70, 80, 90% or more lower than the second one).

Another object of the present invention is a kit for implementing the method of the invention, wherein said kit comprises means for measuring the expression level of at least one cell surface nutrient transporter, preferably XPR1 and/or GLUT1, more preferably XPR1 and GLUT1.

In one embodiment, the expression level of at least one cell surface nutrient transporter is assessed at the RNA level, and the kit of the invention may comprise means for total RNA extraction, means for reverse transcription of total RNA, and means for quantifying the expression of RNA of at least one cell surface nutrient transporter, preferably XPR1 and/or GLUT1. In one embodiment, the means for quantifying the expression of RNA of at least one cell surface nutrient transporter, preferably XPR1 and/or GLUT1 are PCR or qPCR primers specific for said cell surface nutrient transporter, preferably XPR1 and/or GLUT1. Examples of PCT or qPCR primers specific for XPR1 include, but are not limited to, the following couple of primers: Forward primer: 5'-AGAGCTTGGGA-GACAAAGCA-3' (SEQ ID NO: 25)—Reverse primer: 5'-GTGGACACAACATTCGCAAC-3' (SEQ ID NO: 26). Examples of PCT or qPCR primers specific for GLUT1 include, but are not limited to, the following couple of primers: Forward primer: 5'-TCACTGTGCTCCTGGTTCTG-3' (SEQ ID NO: 27)—Reverse primer: 5'-CCTCGGGTGTCTTGTCACTT-3' (SEQ ID NO: 28). In one embodiment, the kit also comprises reagents for carrying out a quantitative PCR (such as, for example, buffers, enzyme, and the like). In one embodiment, the kit of the invention may also comprise means for detecting the expression level of at least one normalization gene at the RNA level.

In another embodiment, the expression level of at least one cell surface nutrient transporter is assessed at the protein level, and the kit of the invention may comprise means for detecting the at least one cell surface nutrient transporter, preferably XPR1 and/or GLUT1. In one embodiment, said means for detecting the at least one cell surface nutrient transporter is an antibody specific of said at least one cell surface nutrient transporter, preferably XPR1 and/or GLUT1. In another embodiment, said means for detecting the at least one cell surface nutrient transporter is a RBD as defined in the present invention and specific of the at least one cell surface nutrient transporter. In one embodiment, the kit of the invention may also comprise means for detecting the expression level of at least one normalization protein.

The present invention also relates to a cell surface nutrient transporter, preferably XPR1 and/or GLUT1, as a biomarker of cell aging (preferably, XPR1 and/or GLUT1 is an early biomarker of cell aging) or senescence, and/or as a biomarker of the accumulation of cell divisions.

The present invention also relates to a cell surface nutrient transporter, preferably XPR1 and/or GLUT1, as a biomarker of the proliferation capacity and/or of the differentiation capacity of a cell. In one embodiment, the cell surface nutrient transporter, preferably XPR1 and/or GLUT1, is a biomarker of stemness.

The present invention also relates to a cell surface nutrient transporter, preferably XPR1 and/or GLUT1, as a biomarker of the quality of a cell batch, in particular of a cell batch to be used in regenerative medicine or a cell batch to be used in in vitro screening assays.

The present invention also relates to an in vitro method of screening compounds impacting cell aging, such as, for example, compounds slowing down (anti-aging effect) or accelerating (pro-aging or pro-senescence effect) cell aging, wherein said screening method comprises determining or measuring the expression level of at least one cell surface nutrient transporter, preferably XPR1 and/or GLUT1, more preferably XPR1.

In one embodiment, the in vitro method is for screening compounds impacting progeroid syndromes, preferably, progeria. Progeroid syndromes and progeria are models of accelerated aging. In one embodiment, the in vitro method is for screening compounds that may be used for treating progeroid syndromes, preferably, for treating progeria, through anti-aging activity.

In one embodiment, the in vitro method is for screening compounds impacting cancer cells. Cancer cells are characterized by their ability to avoid senescence. In one embodiment, the in vitro method is for screening compounds that may be used for treating cancer cells, through pro-senescence (or pro-aging) activity.

In one embodiment, the method of the invention further comprises comparing the measured expression level with a reference expression level.

In one embodiment, the reference expression level is an index value or is derived from one or more risk prediction algorithms or computed indices for the anti- or pro-aging effect of the tested compound. A reference can be relative to a number or value derived from cell population studies, preferably based on cells which are the same as the ones used for testing the anti- or pro-aging effect of said compound, and which are cultured in the same culture medium with the same culture conditions.

In another embodiment of the invention, the reference expression level is derived from the measurement of the expression level in a control cell sample exposed to a compound known not to present a pro- or anti-aging effect. According to this embodiment, a difference between the measured expression level and the reference expression level is indicative of the pro- or anti-aging effect of the tested compound.

In another embodiment of the invention, the reference expression level is derived from the measurement of the expression level in a control cell sample exposed to a compound known to present a pro- or anti-aging effect. According to this embodiment, the absence of difference between the measured expression level and the reference expression level is indicative of the pro- or anti-aging effect of the tested compound.

In one embodiment of the invention, the reference expression level is derived from the measurement of the expression level in a control cell culture in the absence of the tested compound. According to this embodiment, a difference between the measured expression level and the reference expression level is indicative of the pro- or anti-aging effect of the tested compound.

In one embodiment, a culture of cells is provided, and separated in two different culture batches, wherein the first culture batch is exposed to the compound to be tested (for measuring the expression level) and the second culture batch is not exposed to the compound to be tested (for measuring the reference expression level).

BRIEF DESCRIPTION OF THE DRAWINGS

FIG. 1 is a combination of graphs showing the evolution of the ratio XPR1/GLUT1 with cell culture passages (P: passage). (A) Evolution of the doubling time of hESC-SA001 derived MSC with the number of cumulated divisions and culture passages. (B) Evolution of XPR1 (left panel) and GLUT1 (right panel) cell surface expression with the number of cumulated divisions and culture passages. (C) Evolution of the XPR1/GLUT1 ratio with the number of cumulated divisions and culture passages. (D) Evolution of the XPR1 mRNA relative expression level (normalized to GAPDH) with the number of cumulated divisions and culture passages.

EXAMPLES

Figure 2:
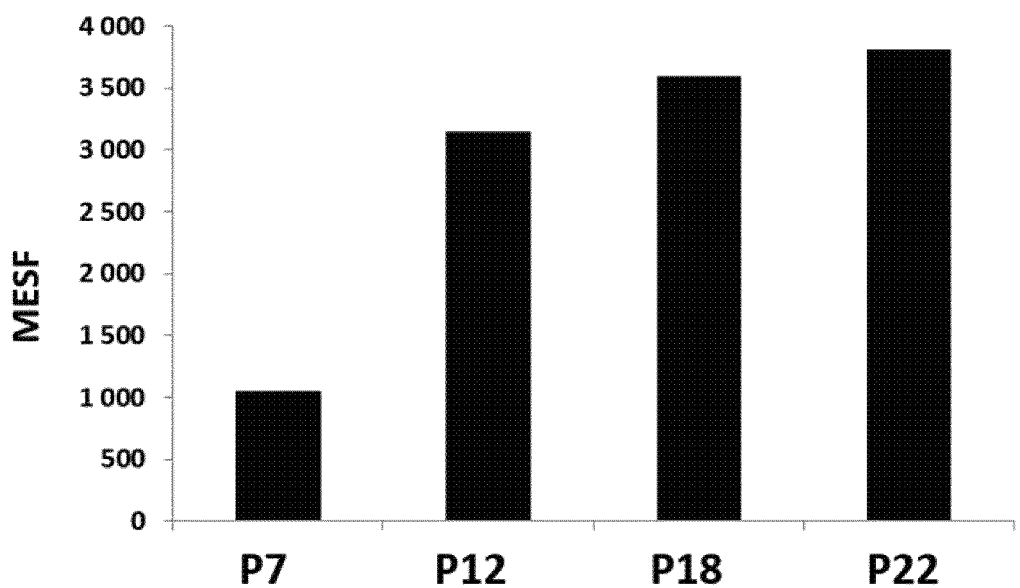
FIG. 2 is a histogram showing the expression of XPR1 according to the number of culture passages (P) in an equine stem cell line. MESF: Molecules of Equivalent Soluble Fluorochrome.

The present invention is further illustrated by the following examples.

Example 1: Signature for Monitoring the Proliferation Potential of Human MSC Material and Method MSCs were detached using TrypLE Express (Life Technologies) for 5 minutes at 37° C. and transferred into a 96-well V-shape microplate. $3 \cdot 10^4$ cells were used for each binding. RBD were premixed pairwise (Glut1.RBD.mouseFc and Xeno.RBD.rabbitFc) in culture medium containing 0.1% sodium azide and 1 mM EDTA. RBD were added to MPCs and incubated at 37° C. for 20 min. Cells were washed once with PBS/2% FCS and then incubated with Alexa Fluor 647 goat anti-rabbit IgG (Invitrogen, 1:400) and R-PE goat anti-mouse IgG1 (Invitrogen, 1:200) antibodies in binding buffer (PBS/2% FCS/0.1% sodium azide/1 mM EDTA), containing 0.3 µg/mL DAPI to restrict the analysis to live cells. After 30 min of incubation at 4° C., cells were washed and resuspended in binding buffer before flow cytometry analysis. Fluorescent signals were acquired on a FACSVerse flow cytometer (BD Biosciences) with 405, 488 and 640 nm excitation, and data analysis was performed using Flowjo software (Tree Star Inc.). Dead cells were excluded from the analysis. "Fluorescence minus one" (FMO) controls were used to establish background levels in RBD channels (R-PE and AF647). Signals were converted into molecules of equivalent soluble fluorochrome (MESF) values using calibration beads (R-PE and AF647 MESF Quantum Beads; Bangs Laboratories) according to the manufacturer's instructions.

Results

As shown in FIG. 1, the expression level of XPR1 increases with cumulated divisions of human MSC derived from embryonic stem cells (SA001 cells). Said increased expression is observed both on cell surface expression (FIG. 1B) and on mRNA expression (FIG. 1D). On the contrary, the expression level of GLUT1 decreases with cumulated divisions (FIG. 1B).

Moreover, as shown in FIG. 1C, the ratio XPR1/GLUT1 increases with cumulated divisions of human MSC derived from embryonic stem cells (SA001 cells).

These results confirm that XPR1, GLUT1 and the ratio XPR1/GLUT1 may be used as biomarkers of cell aging.

Example 2: XPR1 Expression in Equine Stem Cells

Material and Method

MSCs were detached using TrypLE Express (Life Technologies) for 5 minutes at 37° C. and transferred into a 96-well V-shape microplate. $3 \cdot 10^4$ cells were used for each binding. Xeno.RBD.rabbitFc, diluted in culture medium containing 0.1% sodium azide and 1 mM EDTA, was added to MPCs and incubated at 37° C. for 20 min. Cells were washed once with PBS/2% FCS and then incubated with Alexa Fluor 647 goat anti-rabbit IgG (Invitrogen, 1:400) antibody in binding buffer (PBS/2% FCS/0.1% sodium azide/1 mM EDTA), containing 0.3 µg/mL DAPI to restrict the analysis to live cells. After 30 min of incubation at 4° C., cells were washed and resuspended in binding buffer before flow cytometry analysis. Fluorescent signals were acquired on a FACSVerse flow cytometer (BD Biosciences) with 405, 488 and 640 nm excitation, and data analysis was performed using Flowjo software (Tree Star Inc.). Dead cells were excluded from the analysis. "Fluorescence minus one" (FMO) controls were used to establish background level in RBD channel (AF647). Signals were converted into molecules of equivalent soluble fluorochrome (MESF) values using calibration beads (AF647 MESF Quantum Beads; Bangs Laboratories) according to the manufacturer's instructions.

Results

As shown in FIG. 2, the expression level of XPR1 increases with culture passages in equine MSC. This result thus demonstrates that XPR1 is also a potential biomarker of cell aging in equine stem cells.

Example 3: XPR1 Expression and Cell Aging of Bone Marrow—Derived hMSC

Material and Method

Human bone marrow-derived MSCs from 2 donors at different passages (P4, P6 and P8) were thawed and plated at a cell density of 60 cells/cm². Cells were expanded in complete medium containing α-MEM, L-glutamine, P/S and 16.5% lot-selected fetal calf serum. When cultures reached 80% confluence, cells were detached by trypsin (0.25% Trypsin/EDTA, Life Technologies) for 5 minutes at 37° C. and the doubling time (h) was determined by counting each cell batch at each passage.

$3 \cdot 10^4$ cells of each batch at each passage were transferred into a 96-well V-shape microplate for each binding.

Xeno.RBD.rabbitFc was prepared in culture medium containing 0.1% sodium azide and 1 mM EDTA. Xeno.RBD.rFc was added to MSCs and incubated at 37° C. for 20 minutes. Cells were washed once with buffer B (PBS/2% FCS/0.1% sodium azide/1 mM EDTA) and then incubated with Alexa Fluor 647 goat anti-rabbit IgG (Life Technologies, 1/1 000) in buffer B containing 1 μg/mL DAPI to restrict analysis to live cells. After 30 minutes of incubation at 4° C. in the dark, the cells were washed twice and resuspended in buffer B before flow cytometry analysis. Fluorescent signals were acquired on a FACSVerse flow cytometer (BD Biosciences) with 405, 488 and 640 nm excitation, and data analysis was performed using Flowjo software (Tree Star Inc.).

Dead cells were excluded from the analysis. Cells only labelled with the AF647 goat anti-rabbit secondary antibody were used to establish background level. Signals were converted into molecules and equivalent soluble fluorochrome (MESF) values using calibration beads (AF647 MESF Quantum Beads, Bangs Laboratories) according to the manufacturer's instructions.

Data represent the mean+/−SD of a triplicate of labelling of XPR1 and statistical significance was determined using a Student's t-test. $p<0.05$ was considered to be significant.

Results

Figure 3:
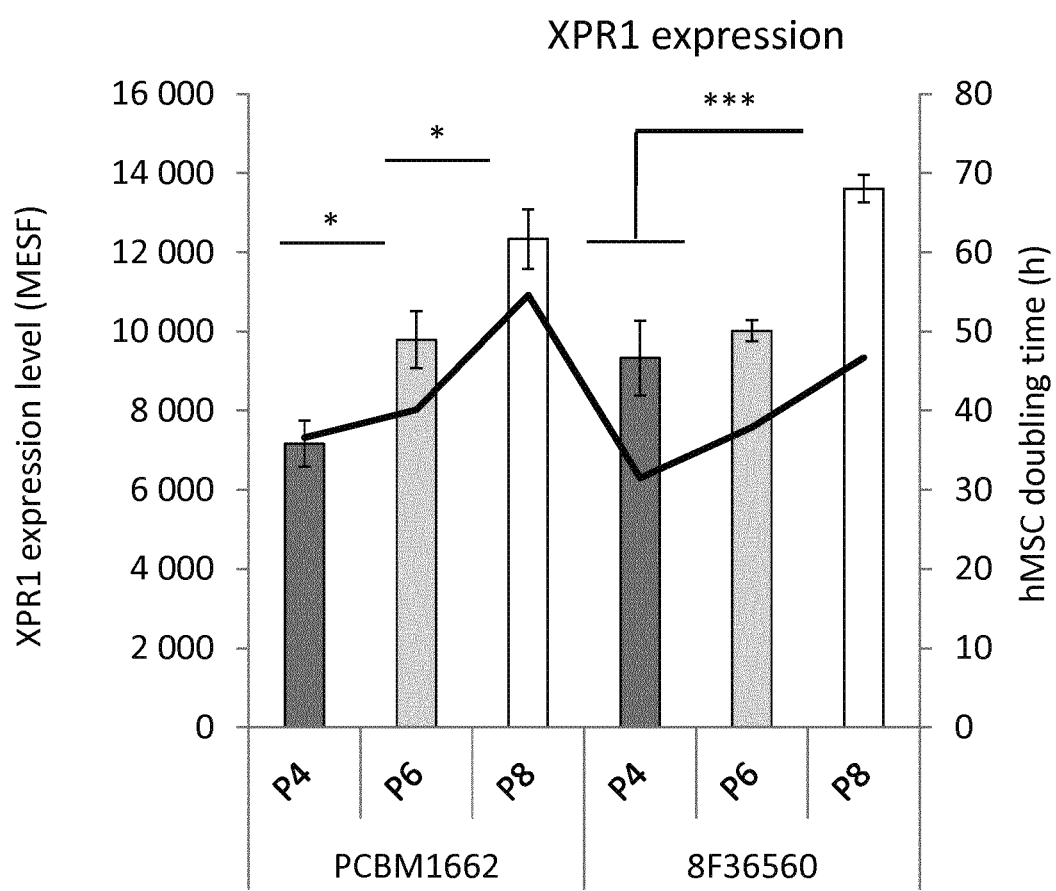
FIG. 3 is a histogram showing the expression of XPR1 according to the number of culture passages (P) in a bone marrow derived hMSC cell line. MESF: Molecules of Equivalent Soluble Fluorochrome. * $p<0.05$; *** $p<0.001$ (Student's t Test).

As shown in FIG. 3, XPR1 expression increases with the number of cell divisions (reflected by the number of passages), and with the doubling time for each donor. Increase of population doubling time indicates that cells are entering into replicative senescence.

These results confirm that XPR1 increase may be used as a biomarker of cell aging in hMSC derived from bone-marrow.

Example 4: XPR1 in a Slow-Down Model of Proliferation Induced by a Reduction of FCS in ES-Derived hMSC Material and Method hMSC derived from Embryonic Stem (ES) cells were cultured in decreasing concentrations of FCS (20, 5 and 1%) that did induce a slow-down in proliferation. When cultures reached 70-80% confluence, cells were detached using TrypLE Express (Life technologies) for 5 minutes at 37° C., and the doubling time (h) was determined by counting before transfer into a 96-well V-shape microplate. $3 \cdot 10^4$ cells were used for each binding. RBDs were premixed pairwise (Glut1.RBD.mouseFc and Xeno.RBD.rabbitFc) in culture medium containing 0.1% sodium azide and 1 mM EDTA. RBDs were added to hMSCs and incubated at 37° C. for 20 minutes. Cells were washed once with buffer B (PBS/2% FCS/0.1% sodium azide/1 mM EDTA) and then incubated with Alexa Fluor 647 goat anti-rabbit IgG (Life Technologies, 1/1 000) and R-PE goat anti-mouse IgG1 (Life technologies, 1/100) in buffer B. After 30 minutes of incubation at 4° C. in the dark, the cells were washed twice and resuspended in buffer B before flow cytometry analysis. Fluorescent signals were acquired on a FACSVerse flow cytometer (BD Biosciences) with 405, 488 and 640 nm excitation, and data analysis was performed using Flowjo software (Tree Star Inc.).

"Fluorescence minus One" controls were used to establish background level (or noise) in RBD channel (R-PE and AF647) and signal/noise represents the expression level of XPR1 and Glut1. Data represent the mean+/−SD (3 replicates).

Results

Figure 4C:
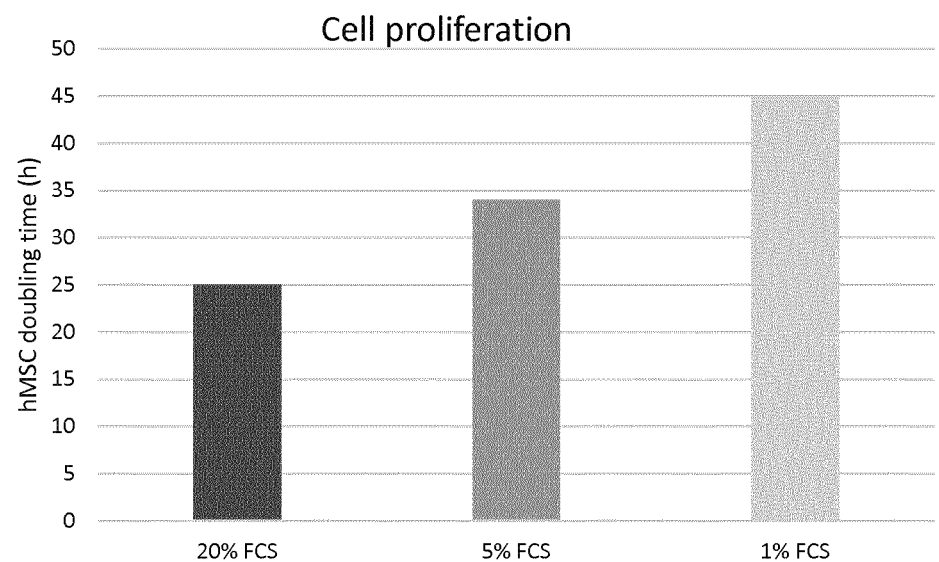
FIG. 4 represents the expression of XPR1 and GLUT1 (A), the ratio XPR1/GLUT1 (B) and cell proliferation (C) in a slow-down model of proliferation induced by a reduction in fetal calf serum.

As shown in FIG. 4A the expression of XPR1 increases with lowering concentrations of FCS. At the opposite, the expression of Glut1 decreases in ES-derived hMSC. In addition, the ratio XPR1/Glut1 increases with lower concentrations of FCS (FIG. 4B). The doubling times (h) increases with lower concentrations of FCS, indicating a slow-down of cell proliferation (FIG. 4C)

Altogether, these data confirm that XPR1, Glut1 and the ratio XPR1/Glut1 may be used as biomarkers of cell proliferation.

Example 5: XPR1 in a Senescence Accelerated-Model Induced by Mitomycin C in ES-Derived hMSC and in an Anti-Aging Model Induced by Rapamycin in ES-Derived hMSC Material and Method
Mitomycin Treatment—

80% confluent hMSCs derived from ES cells were treated for 3 hours with 1 or 10 μg/mL of mitomycin C (MMC, Sigma) or none (control cells). After the pulse of MMC, the cells were washed twice with PBS, detached with TrypLE Express for 5 minutes à 37° C. and re-plated in flasks for 4 additional days at the end of which the cells were detached for RBD labelling and the doubling time (h) was determined by counting.

$3 \cdot 10^4$ cells were used for each binding and were transferred into a 96-well V-shape microplate. RBDs were premixed pairwise (Glut1.RBD.mouseFc and Xeno.RBD.rabbitFc) in culture medium containing 0.1% sodium azide and 1 mM EDTA. RBDs were added to hMSCs and incubated at 37° C. for 20 minutes. Cells were washed once with buffer B (PBS/2% FCS/0.1% sodium azide/1 mM EDTA) and then incubated with Alexa Fluor 647 goat anti-rabbit IgG (Life Technologies, 1/1 000) and R-PE goat anti-mouse IgG1 (Life technologies, 1/100) in buffer B. After 30 minutes of incubation at 4° C. in the dark, the cells were washed twice and resuspended in buffer B before flow cytometry analysis. Fluorescent signals were acquired on a FACSVerse flow cytometer (BD Biosciences) with 405, 488 and 640 nm excitation, and data analysis was performed using Flowjo software (Tree Star Inc.).

"Fluorescence minus One" controls were used to establish background level in RBD channels (R-PE and AF647). Signal/noise of 1 and 10 μg/mL mitomycin c conditions were normalized to control condition.

Rapamycin Treatment—

Rapamycin is described in the literature for preventing in vitro cellular senescence in human cells and to slow aging in mice (Wilkinson, J. E., et al. (2012). Rapamycin slows aging in mice. Aging Cell 11, 675-682).

hMSC derived from ES cells were treated by 0.1 or 10 nM rapamycin (Sigma) 1 day after seeding at 5 000 cells/cm². 0.03% DMSO was used as control. Three days after the treatment, the cells were detached using TrypLE Express (Life technologies) for 5 minutes at 37° C. and transferred into a 96-well V-shape microplate. $3 \cdot 10^4$ cells were used for each binding. RBDs were premixed pairwise (Glut1.RBD.mouseFc and Xeno.RBD.rabbitFc) in culture medium containing 0.1% sodium azide and 1 mM EDTA. RBDs were added to MSCs and incubated at 37° C. for 20 minutes. Cells were washed once with buffer B (PBS/2% FCS/0.1% sodium azide/1 mM EDTA) and then incubated with Alexa Fluor 647 goat anti-rabbit IgG (Life Technologies, 1/1 000) and R-PE goat anti-mouse IgG1 (Life technologies, 1/100) in buffer B. After 30 minutes of incubation at 4° C. in the dark, the cells were washed twice and resuspended in buffer B before flow cytometry analysis. Fluorescent signals were acquired on a FACSVerse flow cytometer (BD Biosciences) with 405, 488 and 640 nm excitation, and data analysis was performed using Flowjo software (Tree Star Inc.).

"Fluorescence minus One" controls were used to establish background level in RBD channels (R-PE and AF647). Signal/noise of 0.1 and 10 nM rapamycin conditions were normalized to control condition.

Result

Figure 5:
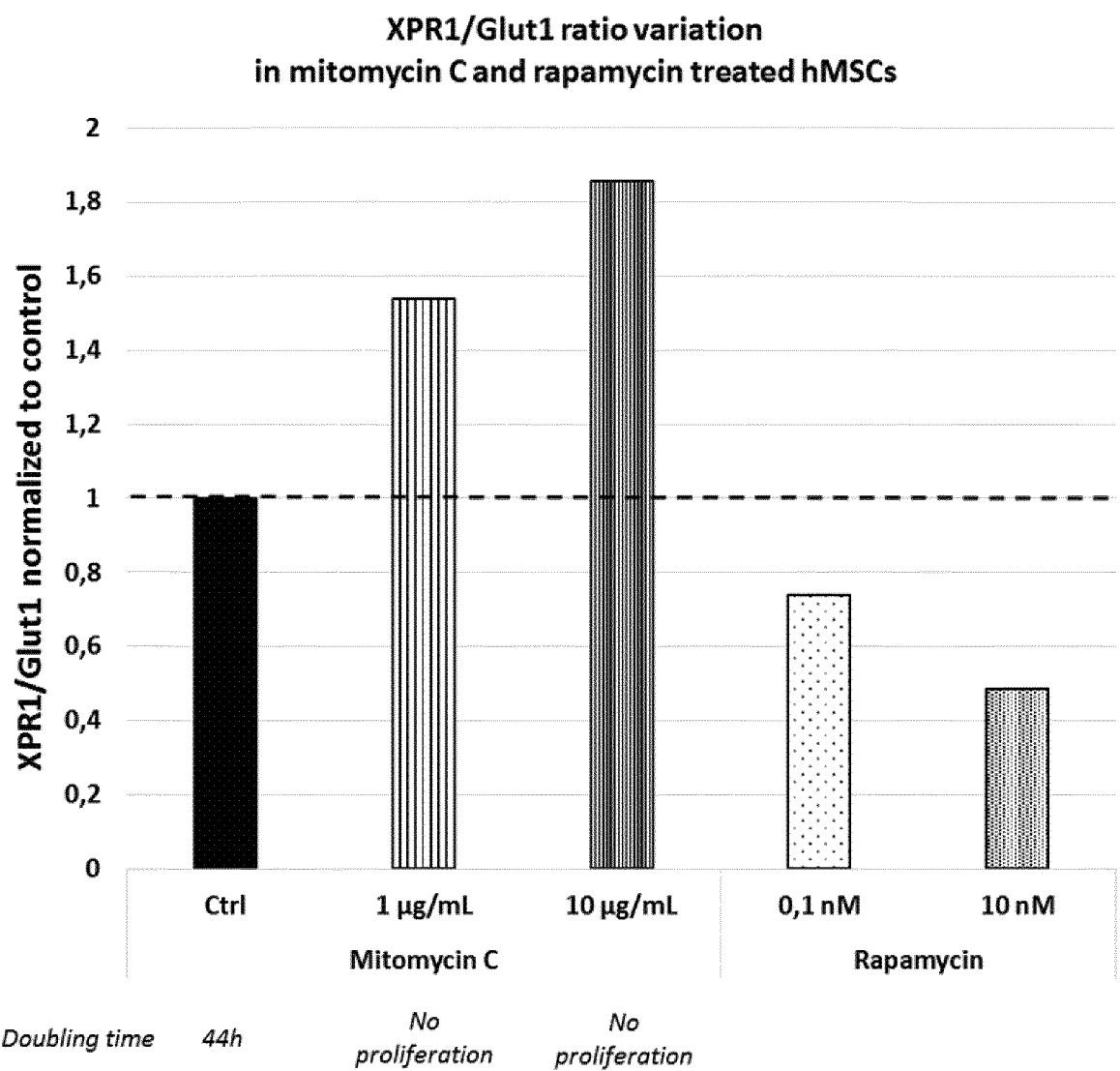
FIG. 5 represents the ratio XPR1/GLUT1 in a senescence accelerated-model of proliferation (mitomycin) and in an anti-aging model (rapamycin).

Data represent XPR1/Glut1 ratio on hMSC treated by 1 or 10 µg/mL of MMC or 0.1 or 10 nM of rapamycin normalized to the control condition (FIG. 5).

The pro-senescence drug Mitomycin C increases the XPR1/Glut1 ratio in a dose-dependant manner which confirms that XPR1/Glut1 ratio is a potential biomarker for accelerated cellular senescence, also called replicative senescence (mitomycin-treated cells are well known to stop cell proliferation).

The anti-aging drug Rapamycin decreases the XPR1/Glut1 ratio in a dose-dependant manner.

These data thus strongly support that the ratio XPR1/Glut1 may be a biomarker for screening and identification of drugs impacting aging, such as, for example, anti-aging drugs or pro-senescence drugs.

The invention claimed is:

1. A method for obtaining at least one cell for administering to a patient in need of regeneration of a renewable tissue, wherein said method comprises:
providing a plurality of mesenchymal stem cells (MSC),
measuring the expression level of a cell surface nutrient transporter of each cell in said plurality of MSC wherein said cell surface nutrient transporter is XPR1;
comparing the measured expression level of each cell with a reference expression level, wherein said reference expression level is the expression level of said cell surface nutrient transporter measured in an old batch of cells, wherein XPR1 expression increases with cell aging;
determining that the expression level of XPR1 of at least one cell of said plurality of MSC is lower than the reference expression level of XPR1 in the old batch of cells; and
selecting the at least one cell from said plurality of MSC; and administering to said patient in need of regeneration of a renewable tissue.

2. The method according to claim 1, wherein said expression level is assessed at the RNA level.

3. The method according to claim 1, wherein said expression level is assessed at the protein level.

4. The method according to claim 1, wherein the measurement of the expression level of said cell surface nutrient transporter corresponds to the detection and quantification of said cell surface nutrient transporter at the protein level on the cell surface.

5. The method according to claim 1, wherein the measurement of the expression level of said cell surface nutrient transporter corresponds to detecting and/or quantifying the binding of a ligand to a cell surface nutrient transporter, wherein said ligand is an antibody or is a receptor binding domain ligand (RBD) comprising a part or the totality of a receptor binding domain (RBD) derived from the soluble part of a glycoprotein of an enveloped virus.

6. The method according to claim 5, wherein said RBD is Xeno.RBD, and comprises or consists of the amino acid sequence SEQ ID NO: 1 or fragments thereof.

7. The method according to claim 1, wherein said reference expression level is a personalized reference, wherein said personalized reference is the expression level of said cell nutrient transporter determined earlier in the same cell and a difference between the measured expression level and said reference expression level is indicative of cell aging.

* * * * *

SEQUENCE LISTING

```
<160> NUMBER OF SEQ ID NOS: 45

<210> SEQ ID NO 1
<211> LENGTH: 316
<212> TYPE: PRT
<213> ORGANISM: Artificial Sequence
<220> FEATURE:
<223> OTHER INFORMATION: Xeno.RBD

<400> SEQUENCE: 1

Met Leu Val Met Glu Gly Ser Ala Phe Ser Lys Pro Leu Lys Asp Lys
1               5                   10                  15

Ile Asn Pro Trp Gly Pro Leu Ile Val Met Gly Ile Leu Val Arg Ala
            20                  25                  30

Gly Ala Ser Val Gln Arg Asp Ser Pro His Gln Ile Phe Asn Val Thr
        35                  40                  45

Trp Arg Val Thr Asn Leu Met Thr Gly Gln Thr Ala Asn Ala Thr Ser
    50                  55                  60

Leu Leu Gly Thr Met Thr Asp Thr Phe Pro Lys Leu Tyr Phe Asp Leu
65                  70                  75                  80

Cys Asp Leu Val Gly Asp Tyr Trp Asp Pro Glu Pro Asp Ile Gly
                85                  90                  95

Asp Gly Cys Arg Thr Pro Gly Gly Arg Arg Thr Arg Leu Tyr Asp
                100                 105                 110

Phe Tyr Val Cys Pro Gly His Thr Val Pro Ile Gly Cys Gly Gly Pro
            115                 120                 125

Gly Glu Gly Tyr Cys Gly Lys Trp Gly Cys Glu Thr Thr Gly Gln Ala
    130                 135                 140

Tyr Trp Lys Pro Ser Ser Ser Trp Asp Leu Ile Ser Leu Lys Arg Gly
145                 150                 155                 160

Asn Thr Pro Lys Asp Gln Gly Pro Cys Tyr Asp Ser Ser Val Ser Ser
                165                 170                 175

Gly Val Gln Gly Ala Thr Pro Gly Gly Arg Cys Asn Pro Leu Val Leu
            180                 185                 190

Glu Phe Thr Asp Ala Gly Arg Lys Ala Ser Trp Asp Ala Pro Lys Val
        195                 200                 205

Trp Gly Leu Arg Leu Tyr Arg Ser Thr Gly Ala Asp Pro Val Thr Arg
    210                 215                 220

Phe Ser Leu Thr Arg Gln Val Leu Asn Val Gly Pro Arg Val Pro Ile
225                 230                 235                 240

Gly Pro Asn Pro Val Ile Thr Asp Gln Leu Pro Pro Ser Gln Pro Val
                245                 250                 255

Gln Ile Met Leu Pro Arg Pro Pro His Pro Pro Pro Ser Gly Thr Val
            260                 265                 270

Ser Met Val Pro Gly Ala Pro Pro Ser Gln Gln Pro Gly Thr Gly
        275                 280                 285
```

```
Asp Arg Leu Leu Asn Leu Val Glu Gly Ala Tyr Gln Ala Leu Asn Leu
    290                 295                 300
Thr Ser Pro Asp Lys Thr Gln Glu Cys Trp Leu Cys
305                 310                 315

<210> SEQ ID NO 2
<211> LENGTH: 296
<212> TYPE: PRT
<213> ORGANISM: Artificial Sequence
<220> FEATURE:
<223> OTHER INFORMATION: Xeno.RBD

<400> SEQUENCE: 2

Met Leu Val Met Glu Gly Ser Ala Phe Ser Lys Pro Leu Lys Asp Lys
1               5                   10                  15
Ile Asn Pro Trp Gly Pro Leu Ile Val Met Gly Ile Leu Val Arg Ala
            20                  25                  30
Gly Ala Ser Val Gln Arg Asp Ser Pro His Gln Ile Phe Asn Val Thr
        35                  40                  45
Trp Arg Val Thr Asn Leu Met Thr Gly Gln Thr Ala Asn Ala Thr Ser
    50                  55                  60
Leu Leu Gly Thr Met Thr Asp Thr Phe Pro Lys Leu Tyr Phe Asp Leu
65                  70                  75                  80
Cys Asp Leu Val Gly Asp Tyr Trp Asp Pro Glu Pro Asp Ile Gly
                85                  90                  95
Asp Gly Cys Arg Thr Pro Gly Gly Arg Arg Thr Arg Leu Tyr Asp
            100                 105                 110
Phe Tyr Val Cys Pro Gly His Thr Val Pro Ile Gly Cys Gly Gly Pro
        115                 120                 125
Gly Glu Gly Tyr Cys Gly Lys Trp Gly Cys Glu Thr Thr Gly Gln Ala
    130                 135                 140
Tyr Trp Lys Pro Ser Ser Ser Trp Asp Leu Ile Ser Leu Lys Arg Gly
145                 150                 155                 160
Asn Thr Pro Lys Asp Gln Gly Pro Cys Tyr Asp Ser Ser Val Ser Ser
                165                 170                 175
Gly Val Gln Gly Ala Thr Pro Gly Gly Arg Cys Asn Pro Leu Val Leu
            180                 185                 190
Glu Phe Thr Asp Ala Gly Arg Lys Ala Ser Trp Asp Ala Pro Lys Val
        195                 200                 205
Trp Gly Leu Arg Leu Tyr Arg Ser Thr Gly Ala Asp Pro Val Thr Arg
    210                 215                 220
Phe Ser Leu Thr Arg Gln Val Leu Asn Val Gly Pro Arg Val Pro Ile
225                 230                 235                 240
Gly Pro Asn Pro Val Ile Thr Asp Gln Leu Pro Pro Ser Gln Pro Val
                245                 250                 255
Gln Ile Met Leu Pro Arg Pro Pro His Pro Pro Ser Gly Thr Val
            260                 265                 270
Ser Met Val Pro Gly Ala Pro Pro Ser Gln Gln Pro Gly Thr Gly
        275                 280                 285
Asp Arg Leu Leu Asn Leu Val Glu
    290                 295

<210> SEQ ID NO 3
<211> LENGTH: 879
<212> TYPE: DNA
<213> ORGANISM: Artificial Sequence
<220> FEATURE:
```

<221> NAME/KEY: source
<222> LOCATION: 1..879
<223> OTHER INFORMATION: /mol_type="unassigned DNA"
      /note="Xeno.RBD"
      /organism="Artificial Sequence"

<400> SEQUENCE: 3

```
atggaaggtt cagcgttctc aaaacccctt a 165                 170                 175
Thr Gln Pro Pro Pro Thr Ser Pro Pro Leu Val His Asp Ser Asp Leu
            180                 185                 190

Glu His Val Leu Thr Pro Ser Thr Ser Trp Thr Thr Lys Ile Leu Lys
        195                 200                 205

Phe Ile Gln Leu Thr Leu Gln Ser Thr Asn Tyr Ser Cys Met Val Cys
    210                 215                 220

<210> SEQ ID NO 5
<211> LENGTH: 178
<212> TYPE: PRT
<213> ORGANISM: Artificial Sequence
<220> FEATURE:
<223> OTHER INFORMATION: HTLV2.RBD

<400> SEQUENCE: 5

Met Gly Asn Val Phe Phe Leu Leu Leu Phe Ser Leu Thr His Phe Pro
1               5                   10                  15

Leu Ala Gln Gln Ser Arg Cys Thr Leu Thr Val Gly Ile Ser Ser Tyr
            20                  25                  30

His Ser Ser Pro Cys Ser Pro Thr Gln Pro Val Cys Thr Trp Asn Leu
        35                  40                  45

Asp Leu Asn Ser Leu Thr Thr Asp Gln Arg Leu His Pro Pro Cys Pro
    50                  55                  60

Asn Leu Ile Thr Tyr Ser Gly Phe His Lys Thr Tyr Ser Leu Tyr Leu
65                  70                  75                  80

Phe Pro His Trp Ile Lys Lys Pro Asn Arg Gln Gly Leu Gly Tyr Tyr
                85                  90                  95

Ser Pro Ser Tyr Asn Asp Pro Cys Ser Leu Gln Cys Pro Tyr Leu Gly
            100                 105                 110

Cys Gln Ser Trp Thr Cys Pro Tyr Thr Gly Pro Val Ser Ser Pro Ser
        115                 120                 125

Trp Lys Phe His Ser Asp Val Asn Phe Thr Gln Glu Val Ser Gln Val
    130                 135                 140

Ser Leu Arg Leu His Phe Ser Lys Cys Gly Ser Ser Met Thr Leu Leu
145                 150                 155                 160

Val Asp Ala Pro Gly Tyr Asp Pro Leu Trp Phe Ile Thr Ser Glu Pro
                165                 170                 175

Thr Gln

<210> SEQ ID NO 6
<211> LENGTH: 534
<212> TYPE: DNA
<213> ORGANISM: Artificial Sequence
<220> FEATURE:
<221> NAME/KEY: source
<222> LOCATION: 1..534
<223> OTHER INFORMATION: /mol_type="unassigned DNA"
      /note="HTLV2.RBD"
      /organism="Artificial Sequence"

<400> SEQUENCE: 6
atgggtaatg tttcttcct acttttattc agtctcacac attttccact agcccagcag      60
agccgatgca cactcacagt tggtatctcc tcctaccact ccagcccctg tagcccaacc     120
caacccgtct gcacgtggaa cctcgacctt aattccctaa caacggacca acgactacac     180 ccccctgcc ctaacctaat tacttactct ggcttccata agacttattc cttatactta     240
ttcccacatt ggataaaaaa gccaaacaga cagggcctag gtactactc gccttcctac     300

|  |  |  |  |  | |
|---|---|---|---|---|---|
| aatgaccctt | gctcgctaca | atgcccctac | ttgggctgcc | aatcatggac | atgcccatac | 360 |
| acgggccccg | tctccagtcc | atcctggaag | tttcattcag | atgtaaattt | cacccaggaa | 420 |
| gtcagccaag | tgtcccttcg | actacacttc | tctaagtgcg | gctcctccat | gaccctccta | 480 |
| gtagatgccc | tggatatga | tcctttatgg | ttcatcacct | cagaacccac | tcag | 534 |

<210> SEQ ID NO 7
<211> LENGTH: 228
<212> TYPE: PRT
<213> ORGANISM: Artificial Sequence
<220> FEATURE:
<223> OTHER INFORMATION: HTLV1.RBD

<400> SEQUENCE: 7

Met Gly Lys Phe Leu Ala Thr Leu Ile Leu Phe Phe Gln Phe Cys Pro
1               5                   10                  15

Leu Ile Phe Gly Asp Tyr Ser Pro Ser Cys Cys Thr Leu Thr Ile Gly
            20                  25                  30

Val Ser Ser Tyr His Ser Lys Pro Cys Asn Pro Ala Gln Pro Val Cys
        35                  40                  45

Ser Trp Thr Leu Asp Leu Leu Ala Leu Ser Ala Asp Gln Ala Leu Gln
    50                  55                  60

Pro Pro Cys Pro Asn Leu Val Ser Tyr Ser Ser Tyr His Ala Thr Tyr
65                  70                  75                  80

Ser Leu Tyr Leu Phe Pro His Trp Thr Lys Lys Pro Asn Arg Asn Gly
                85                  90                  95

Gly Gly Tyr Tyr Ser Ala Ser Tyr Ser Asp Pro Cys Ser Leu Lys Cys
            100                 105                 110

Pro Tyr Leu Gly Cys Gln Ser Trp Thr Cys Pro Tyr Thr Gly Ala Val
        115                 120                 125

Ser Ser Pro Tyr Trp Lys Phe Gln His Asp Val Asn Phe Thr Gln Glu
    130                 135                 140

Val Ser Arg Leu Asn Ile Asn Leu His Phe Ser Lys Cys Gly Phe Pro
145                 150                 155                 160

Phe Ser Leu Leu Val Asp Ala Pro Gly Tyr Asp Pro Ile Trp Phe Leu
                165                 170                 175

Asn Thr Glu Pro Ser Gln Leu Pro Pro Thr Ala Pro Leu Leu Pro
            180                 185                 190

His Ser Asn Leu Asp His Ile Leu Glu Pro Ser Ile Pro Trp Lys Ser
        195                 200                 205

Lys Leu Leu Thr Leu Val Gln Leu Thr Leu Gln Ser Thr Asn Tyr Thr
    210                 215                 220

Cys Ile Val Cys
225

<210> SEQ ID NO 8
<211> LENGTH: 224
<212> TYPE: PRT
<213> ORGANISM: Artificial Sequence
<220> FEATURE:
<223> OTHER INFORMATION: HTLV4.RBD

<400> SEQUENCE: 8

Met Gly Asn Val Leu Phe Leu Thr Leu Leu Ala Thr Leu Gly Ile Pro
1               5                   10                  15

Val Leu Gln Ala Ser Arg Cys Thr Ile Thr Val Gly Ile Ser Ser Tyr
            20                  25                  30

-continued

His Ser Ser Pro Cys Ser Pro Ala Gln Pro Leu Cys Thr Trp Ala Leu
         35                  40                  45

Asp Leu Val Ser Ile Thr Lys Asp Gln Leu Leu Tyr Pro Pro Cys Gln
 50                  55                  60

Asn Leu Ile Thr Tyr Ser Asn Tyr His Lys Thr Tyr Ser Leu Tyr Leu
 65                  70                  75                  80

Phe Pro His Trp Val Gln Lys Pro Leu Arg Arg Gly Leu Gly Tyr Tyr
                 85                  90                  95

Ser Ala Ser Tyr Ser Asp Pro Cys Ser Leu Gln Cys Pro Tyr Leu Gly
            100                 105                 110

Ser Gln Ser Trp Thr Cys Pro Tyr Thr Gly Pro Val Ser Ser Pro Thr
            115                 120                 125

Trp Arg Phe Ser Thr Asp Val Asn Phe Thr Gln Glu Val Ser Arg Val
        130                 135                 140

Ser Leu Lys Leu His Phe Ser Lys Cys Gly Ser Ser Leu Thr Leu Leu
145                 150                 155                 160

Ile Asp Ala Pro Gly Tyr Asp Pro Leu Trp Tyr Leu Thr Ser Glu Pro
                165                 170                 175

Thr Gln Glu Pro Pro Thr Pro Pro Leu Val Ser Asp Ser Asp Leu
            180                 185                 190

Glu His Val Leu Thr Pro Ser Ala Ser Trp Ala Ser Lys Met Leu Thr
            195                 200                 205

Leu Ile His Leu Thr Leu Gln Ser Thr Asn Tyr Ser Cys Met Val Cys
        210                 215                 220

<210> SEQ ID NO 9
<211> LENGTH: 228
<212> TYPE: PRT
<213> ORGANISM: Artificial Sequence
<220> FEATURE:
<223> OTHER INFORMATION: Rabbit Fc fragment

<400> SEQUENCE: 9

Ala Pro Ser Thr Cys Ser Lys Pro Thr Cys Pro Pro Glu Leu Leu
1               5                   10                  15

Gly Gly Pro Ser Val Phe Ile Phe Pro Pro Lys Pro Lys Asp Thr Leu
             20                  25                  30

Met Ile Ser Arg Thr Pro Glu Val Thr Cys Val Val Asp Val Ser
         35                  40                  45

Gln Asp Asp Pro Glu Val Gln Phe Thr Trp Tyr Ile Asn Asn Glu Gln
 50                  55                  60

Val Arg Thr Ala Arg Pro Pro Leu Arg Glu Gln Gln Phe Asp Cys Thr
 65                  70                  75                  80

Ile Arg Val Val Ser Thr Leu Pro Ile Ala His Gln Asp Trp Leu Arg
                 85                  90                  95

Gly Lys Glu Phe Lys Cys Lys Val His Asn Lys Ala Leu Pro Ala Pro
            100                 105                 110

Ile Glu Lys Thr Ile Ser Lys Ala Arg Gly Gln Pro Leu Glu Pro Lys
            115                 120                 125

Val Tyr Thr Met Gly Pro Pro Arg Glu Glu Leu Ser Ser Arg Ser Val
        130                 135                 140

Ser Leu Thr Cys Met Ile Asn Gly Phe Tyr Pro Ser Asp Ile Ser Val
145                 150                 155                 160

Glu Trp Glu Lys Asn Gly Lys Ala Glu Asp Asn Tyr Lys Thr Thr Pro
                165                 170                 175

```
Ala Val Leu Asp Ser Asp Gly Ser Tyr Phe Leu Tyr Ser Lys Leu Ser
            180                 185                 190

Val Pro Thr Ser Glu Trp Gln Arg Gly Asp Val Phe Thr Cys Ser Val
            195                 200                 205

Met His Glu Ala Leu His Asn His Tyr Thr Gln Lys Ser Ile Ser Arg
    210                 215                 220

Ser Pro Gly Lys
225

<210> SEQ ID NO 10
<211> LENGTH: 687
<212> TYPE: DNA
<213> ORGANISM: Artificial Sequence
<220> FEATURE:
<221> NAME/KEY: source
<222> LOCATION: 1..687
<223> OTHER INFORMATION: /mol_type="unassigned DNA"
      /note="Rabbit Fc fragment"
      /organism="Artificial Sequence"

<400> SEQUENCE: 10
gcaccctcga catgcagcaa gcccacgtgc ccaccccctg aactcctggg gggaccgtct      60
gtcttcatct tccccccaaa acccaaggac accctcatga tctcacgcac ccccgaggtc     120
acatgcgtgg tggtggacgt gagccaggat gaccccgagg tgcagttcac atggtacata     180
aacaacgagc aggtgcgcac ccgcccggcc ccgctacggg agcagcagtt caacagcacg     240
atccgcgtgg tcagcaccct ccccatcacg caccaggact ggctgagggg caaggagttc     300
aagtgcaaag tccacaacaa ggcactcccg gccccatcg agaaaaccat ctccaaagcc      360
agagggcagc ccctggagcc gaaggtctac accatgggcc ctccccggga ggagctgagc     420
agcaggtcgg tcagcctgac ctgcatgatc aacggcttct acccttccga catctcggtg     480
gagtgggaga gaacgggaa ggcagaggac aactacaaga ccacgccggc cgtgctggac      540
agcgacggct cctacttcct ctacaacaag ctctcagtgc ccacgagtga gtggcagcgg     600
ggcgacgtct tcacctgctc cgtgatgcac gaggccttgc acaaccacta cacgcagaag     660
tccatctccc gctctccggg taaatga                                         687

<210> SEQ ID NO 11
<211> LENGTH: 229
<212> TYPE: PRT
<213> ORGANISM: Artificial Sequence
<220> FEATURE:
<223> OTHER INFORMATION: Mouse Fc fragment

<400> SEQUENCE: 11

Val Asp Val Pro Arg Asp Cys Gly Cys Lys Pro Cys Ile Cys Thr Val
1               5                   10                  15

Pro Glu Val Ser Ser Val Phe Ile Phe Pro Pro Lys Pro Lys Asp Val
            20                  25                  30

Leu Thr Ile Thr Leu Thr Pro Lys Val Thr Cys Val Val Val Asp Ile
        35                  40                  45

Ser Lys Asp Asp Pro Glu Val Gln Phe Ser Trp Phe Val Asp Asp Val
    50                  55                  60

Glu Val His Thr Ala Gln Thr Gln Pro Arg Glu Glu Gln Phe Asn Ser
65                  70                  75                  80

Thr Phe Arg Ser Val Ser Glu Leu Pro Ile Met His Gln Asp Trp Leu
                85                  90                  95
```

| | | | | | | | | | | | |
|---|---|---|---|---|---|---|---|---|---|---|---|
|Asn|Gly|Lys|Glu|Phe|Lys|Cys|Arg|Val|Asn|Ser|Ala|Ala|Phe|Pro|Ala|
| | | |100| | |105| | | |110| | | | | |

| | | | | | | | | | | | |
|---|---|---|---|---|---|---|---|---|---|---|---|
|Pro|Ile|Glu|Lys|Thr|Ile|Ser|Lys|Thr|Lys|Gly|Arg|Pro|Lys|Ala|Pro|
| |115| | | | |120| | | | |125| | | | |

| | | | | | | | | | | | |
|---|---|---|---|---|---|---|---|---|---|---|---|
|Gln|Val|Tyr|Thr|Ile|Pro|Pro|Pro|Lys|Glu|Gln|Met|Ala|Lys|Asp|Lys|
| |130| | | | |135| | | |140| | | | | |

Val Ser Leu Thr Cys Met Ile Thr Asp Phe Phe Pro Glu Asp Ile Thr
145                 150                 155                 160

Val Glu Trp Gln Trp Asn Gly Gln Pro Ala Glu Asn Tyr Lys Asn Thr
                165                 170                 175

Gln Pro Ile Met Asp Thr Asp Gly Ser Tyr Phe Val Tyr Ser Lys Leu
            180                 185                 190

Asn Val Gln Lys Ser Asn Trp Glu Ala Gly Asn Thr Phe Thr Cys Ser
            195                 200                 205

Val Leu His Glu Gly Leu His Asn His His Thr Glu Lys Ser Leu Ser
210                 215                 220

His Ser Pro Gly Lys
225

```
<210> SEQ ID NO 12
<211> LENGTH: 690
<212> TYPE: DNA
<213> ORGANISM: Artificial Sequence
<220> FEATURE:
<221> NAME/KEY: source
<222> LOCATION: 1..690
<223> OTHER INFORMATION: /mol_type="unassigned DNA"
      /note="Mouse Fc fragment"
      /organism="Artificial Sequence"

<400> SEQUENCE: 12
gtcgacgtgc ccagggattg tggttgtaag ccttgcatat gtacagtccc agaagtatca    60
tctgtcttca tcttcccccc aaagcccaag gatgtgctca ccattactct gactcctaag   120
gtcacgtgtg ttgtggtaga catcagcaag gatgatcccg aggtccagtt cagctggttt   180
gtagatgatg tggaggtgca cacagctcag acgcaacccc gggaggagca gttcaacagc   240
actttccgct cagtcagtga acttcccatc atgcaccagg actggctcaa tggcaaggag   300
ttcaaatgca gggtcaacag tgcagctttc cctgccccca tcgagaaaac catctccaaa   360
accaaaggca gaccgaaggc tccacaggtg tacaccattc cacctcccaa ggagcagatg   420
gccaaggata agtcagtctg acctgcatg ataacagact tcttccctga agacattact    480
gtggagtggc agtggaatgg gcagccagcg gagaactaca gaacactca gcccatcatg    540 gacacagatg gctcttactt cgtctacagc aagctcaatg tgcagaagag caactgggag   600
gcaggaaata ctttcacctg ctctgtgtta catgagggcc tgcacaacca ccatactgag   660
aagagcctct cccactctcc tggtaaatga                                     690

<210> SEQ ID NO 13
<211> LENGTH: 1230
<212> TYPE: DNA
<213> ORGANISM: Artificial Sequence
<220> FEATURE:
<221> NAME/KEY: source
<222> LOCATION: 1..1230
<223> OTHER INFORMATION: /mol_type="unassigned DNA"
      /note="HTLV2.RBD fused to a mouse Fc fragment"
      /organism="Artificial Sequence"

<400> SEQUENCE: 13
```

```
atgggtaatg tttctttcct acttttattc agtctcacac attttccact agcccagcag    60
agccgatgca cactcacagt tggtatctcc tcctaccact ccagcccctg tagcccaacc   120
caacccgtct gcacgtggaa cctcgacctt aattccctaa caacggacca acgactacac   180 ccccctgcc ctaacctaat tacttactct ggcttccata agacttattc cttatactta    240
ttcccacatt ggataaaaaa gccaaacaga cagggcctag ggtactactc gccttcctac   300
aatgacccct gctcgctaca atgccccctac ttgggctgcc aatcatggac atgcccatac  360
acgggccccg tctccagtcc atcctggaag tttcattcag atgtaaattt cacccaggaa   420
gtcagccaag tgtcccttcg actacacttc tctaagtgcg gctcctccat gaccctccta   480
gtagatgccc ctggatatga tcctttatgg ttcatcacct cagaacccac tcagggatcc   540
gtcgacgtgc ccaggattg tggttgtaag ccttgcatat gtacagtccc agaagtatca    600
tctgtcttca tcttcccccc aaagcccaag gatgtgctca ccattactct gactcctaag   660
gtcacgtgtg ttgtggtaga catcagcaag gatgatcccg aggtccagtt cagctggttt   720
gtagatgatg tggaggtgca cacagctcag acgcaacccc gggaggagca gttcaacagc   780
actttccgct cagtcagtga acttcccatc atgcaccagg actggctcaa tggcaaggag   840
ttcaaatgca gggtcaacag tgcagctttc cctgccccca tcgagaaaac catctccaaa   900
accaaaggca gaccgaaggc tccacaggtg tacaccattc cacctcccaa ggagcagatg   960
gccaaggata aagtcagtct gacctgcatg ataacagact tcttccctga agacattact  1020
gtggagtggc agtggaatgg gcagccagcg gagaactaca agaacactca gcccatcatg  1080
gacacagatg gctcttactt cgtctacagc aagctcaatg tgcagaagag caactgggag  1140
gcaggaaata ctttcacctg ctctgtgtta catgagggcc tgcacaacca ccatactgag  1200
aagagcctct cccactctcc tggtaaatga                                   1230

<210> SEQ ID NO 14
<211> LENGTH: 1572
<212> TYPE: DNA
<213> ORGANISM: Artificial Sequence
<220> FEATURE:
<221> NAME/KEY: source
<222> LOCATION: 1..1572
<223> OTHER INFORMATION: /mol_type="unassigned DNA"
     /note="Xeno.RBD fused to a rabbit Fc fragment"
     /organism="Artificial Sequence"

<400> SEQUENCE: 14
atggaaggtt cagcgttctc aaaacccctt aaagataaga ttaacccgtg gggccccta    60 atagttatgg ggatcttggt gagggcagga gcctcggtac aacgtgacag ccctcaccag  120
atcttcaatg ttacttggag agttaccaac ctaatgacag acaaacagc taacgccacc   180 tccctcctgg ggacgatgac agacaccttc cctaaactat attttgacct gtgtgattta  240
gtaggagact actgggatga cccagaaccc gatattgggg atggttgccg cactcccggg  300
ggaagaagaa ggacaagact gtatgacttc tatgtttgcc ccggtcatac tgtaccaata  360
gggtgtggag ggccgggaga gggctactgt ggcaaatggg gatgtgagac cactggacag  420
gcatactgga agccatcatc atcatgggac ctaatttccc ttaagcgagg aaacactcct  480
aaggatcagg gcccctgtta tgattcctcg gtctccagtg gcgtccaggg tgccacaccg  540
gggggtcgat gcaaccccct ggtcttagaa ttcactgacg cgggtagaaa ggccagctgg  600
gatgccccca agtttgggg actaagactc tatcgatcca caggggccga cccggtgacc   660
cggttctctt tgacccgcca ggtcctcaat gtaggacccc gcgtccccat ggggcctaat  720
```

-continued

```
cccgtgatca ctgaccagct acccccatcc caacccgtgc agatcatgct ccccaggcct    780
cctcatcctc ctccttcagg cacggtctct atggtacctg gggctccccc gccttctcaa    840
caacctggga cgggagacag gctgctaaat ctggtagaag gatccgcacc ctcgacatgc    900
agcaagccca cgtgcccacc ccctgaactc tggggggac cgtctgtctt catcttcccc    960
ccaaaaccca aggacaccct catgatctca cgcaccccg aggtcacatg cgtggtggtg   1020
gacgtgagcc aggatgaccc cgaggtgcag ttcacatggt acataaacaa cgagcaggtg   1080
cgcaccgccc ggccgccgct acgggagcag cagttcgact gcacgatccg cgtggtcagc   1140
accctcccca tcgcgcacca ggactggctg agggggcaagg agttcaagtg caaagtccac   1200
aacaaggcac tcccggcccc catcgagaaa accatctcca aagccagagg gcagcccctg   1260
gagccgaagg tctacaccat gggccctccc cgggaggagc tgagcagcag gtcggtcagc   1320
ctgacctgca tgatcaacgg cttctaccct tccgacatct cggtggagtg ggagaagaac   1380
gggaaggcag aggacaacta caagaccacg ccggccgtgc tggacagcga cggctcctac   1440
ttcctctaca gcaagctctc agtgcccacg agtgagtggc agcggggcga cgtcttcacc   1500
tgctccgtga tgcacgaggc cttgcacaac cactacacgc agaagtccat ctcccgctct   1560
ccgggtaaat ga                                                       1572
```

```
<210> SEQ ID NO 15
<211> LENGTH: 20
<212> TYPE: PRT
<213> ORGANISM: Artificial Sequence
<220> FEATURE:
<223> OTHER INFORMATION: human IL-2 peptide signal

<400> SEQUENCE: 15

Met Tyr Arg Met Gln Leu Leu Ser Cys Ile Ala Leu Ser Leu Ala Leu
1               5                   10                  15

Val Thr Asn Ser
            20

<210> SEQ ID NO 16
<211> LENGTH: 18
<212> TYPE: PRT
<213> ORGANISM: Artificial Sequence
<220> FEATURE:
<223> OTHER INFORMATION: human albumin peptide signal

<400> SEQUENCE: 16

Met Lys Trp Val Thr Phe Ile Ser Leu Leu Phe Leu Phe Ser Ser Ala
1               5                   10                  15

Tyr Ser

<210> SEQ ID NO 17
<211> LENGTH: 18
<212> TYPE: PRT
<213> ORGANISM: Artificial Sequence
<220> FEATURE:
<223> OTHER INFORMATION: human chymotrypsinogen peptide signal

<400> SEQUENCE: 17

Met Ala Phe Leu Trp Leu Leu Ser Cys Trp Ala Leu Leu Gly Thr Thr
1               5                   10                  15

Phe Gly

<210> SEQ ID NO 18
```

```
<211> LENGTH: 15
<212> TYPE: PRT
<213> ORGANISM: Artificial Sequence
<220> FEATURE:
<223> OTHER INFORMATION: human trypsinogen-2 peptide signal

<400> SEQUENCE: 18

Met Asn Leu Leu Leu Ile Leu Thr Phe Val Ala Ala Val Ala
1               5                   10                  15

<210> SEQ ID NO 19
<211> LENGTH: 17
<212> TYPE: PRT
<213> ORGANISM: Artificial Sequence
<220> FEATURE:
<223> OTHER INFORMATION: gaussia luciferase peptide signal

<400> SEQUENCE: 19

Met Gly Val Lys Val Leu Phe Ala Leu Ile Cys Ile Ala Val Ala Glu
1               5                   10                  15

Ala

<210> SEQ ID NO 20
<211> LENGTH: 21
<212> TYPE: PRT
<213> ORGANISM: Artificial Sequence
<220> FEATURE:
<223> OTHER INFORMATION: mouse IgM peptide signal

<400> SEQUENCE: 20

Met Lys Phe Ser Trp Val Met Phe Phe Leu Met Ala Val Val Thr Gly
1               5                   10                  15

Val Asn Ser Glu Phe
            20

<210> SEQ ID NO 21
<211> LENGTH: 631
<212> TYPE: PRT
<213> ORGANISM: Homo sapiens

<400> SEQUENCE: 21

Met Lys Phe Ala Glu His Leu Ser Ala His Ile Thr Pro Glu Trp Arg
1               5                   10                  15

Lys Gln Tyr Ile Gln Tyr Glu Ala Phe Lys Asp Met Leu Tyr Ser Ala
                20                  25                  30

Gln Asp Gln Ala Pro Ser Val Glu Val Thr Asp Glu Asp Thr Val Lys
            35                  40                  45

Arg Tyr Phe Ala Lys Phe Glu Glu Lys Phe Gln Thr Cys Glu Lys
    50                  55                  60

Glu Leu Ala Lys Ile Asn Thr Phe Tyr Ser Glu Lys Leu Ala Glu Ala
65                  70                  75                  80

Gln Arg Arg Phe Ala Thr Leu Gln Asn Glu Leu Gln Ser Ser Leu Asp
                85                  90                  95

Ala Gln Lys Glu Ser Thr Gly Val Thr Thr Leu Arg Gln Arg Lys
            100                 105                 110

Pro Val Phe His Leu Ser His Glu Glu Arg Val Gln His Arg Asn Ile
        115                 120                 125

Lys Asp Leu Lys Leu Ala Phe Ser Glu Phe Tyr Leu Ser Leu Ile Leu
    130                 135                 140

Leu Gln Asn Tyr Gln Asn Leu Asn Phe Thr Gly Phe Arg Lys Ile Leu
145                 150                 155                 160
```

```
Lys Lys His Asp Lys Ile Leu Glu Thr Ser Arg Gly Ala Asp Trp Arg
            165                 170                 175
Val Ala His Val Glu Val Ala Pro Phe Tyr Thr Cys Lys Lys Ile Asn
            180                 185                 190
Gln Leu Ile Ser Glu Thr Glu Ala Val Val Thr Asn Glu Leu Glu Asp
            195                 200                 205
Gly Asp Arg Gln Lys Ala Met Lys Arg Leu Arg Val Pro Pro Leu Gly
210                 215                 220
Ala Ala Gln Pro Ala Pro Ala Trp Thr Thr Phe Arg Val Gly Leu Phe
225                 230                 235                 240
Cys Gly Ile Phe Ile Val Leu Asn Ile Thr Leu Val Leu Ala Ala Val
            245                 250                 255
Phe Lys Leu Glu Thr Asp Arg Ser Ile Trp Pro Leu Ile Arg Ile Tyr
            260                 265                 270
Arg Gly Gly Phe Leu Leu Ile Glu Phe Leu Phe Leu Leu Gly Ile Asn
            275                 280                 285
Thr Tyr Gly Trp Arg Gln Ala Gly Val Asn His Val Leu Ile Phe Glu
            290                 295                 300
Leu Asn Pro Arg Ser Asn Leu Ser His Gln His Leu Phe Glu Ile Ala
305                 310                 315                 320
Gly Phe Leu Gly Ile Leu Trp Cys Leu Ser Leu Leu Ala Cys Phe Phe
            325                 330                 335
Ala Pro Ile Ser Val Ile Pro Thr Tyr Val Tyr Pro Leu Ala Leu Tyr
            340                 345                 350
Gly Phe Met Val Phe Leu Ile Asn Pro Thr Lys Thr Phe Tyr Tyr
            355                 360                 365
Lys Ser Arg Phe Trp Leu Leu Lys Leu Leu Phe Arg Val Phe Thr Ala
            370                 375                 380
Pro Phe His Lys Val Gly Phe Ala Asp Phe Trp Leu Ala Asp Gln Leu
385                 390                 395                 400
Asn Ser Leu Ser Val Ile Leu Met Asp Leu Glu Tyr Met Ile Cys Phe
            405                 410                 415
Tyr Ser Leu Glu Leu Lys Trp Asp Glu Ser Lys Gly Leu Leu Pro Asn
            420                 425                 430
Asn Ser Glu Glu Arg Gly His Ser Asp Thr Met Val Phe Phe Tyr Leu
            435                 440                 445
Trp Ile Val Phe Tyr Ile Ile Ser Ser Cys Tyr Thr Leu Ile Trp Asp
            450                 455                 460
Leu Lys Met Asp Trp Gly Leu Phe Asp Lys Asn Ala Gly Glu Asn Thr
465                 470                 475                 480
Phe Leu Arg Glu Glu Ile Val Tyr Pro Gln Lys Ala Tyr Tyr Tyr Cys
            485                 490                 495
Ala Ile Ile Glu Asp Val Ile Leu Arg Phe Ala Trp Thr Ile Gln Ile
            500                 505                 510
Ser Ile Thr Ser Thr Thr Leu Leu Pro His Ser Gly Asp Ile Ile Ala
            515                 520                 525
Thr Val Phe Ala Pro Leu Glu Val Phe Arg Arg Phe Val Trp Asn Phe
            530                 535                 540
Phe Arg Leu Glu Asn Glu His Leu Asn Asn Cys Gly Glu Phe Arg Ala
545                 550                 555                 560
Val Arg Asp Ile Ser Val Ala Pro Leu Asn Ala Asp Asp Gln Thr Leu
            565                 570                 575
```

| | | | | | | | | | | | |
|---|---|---|---|---|---|---|---|---|---|---|---|
|Leu|Glu|Gln|Met|Met|Asp|Gln|Asp|Asp|Gly|Val|Arg|Asn|Arg|Gln|Lys|
| | | |580| | | |585| | | |590| | | | |
|Asn|Arg|Ser|Trp|Lys|Tyr|Asn|Gln|Ser|Ile|Ser|Leu|Arg|Arg|Pro|Arg|
| | |595| | | | |600| | | | |605| | | |
|Leu|Ala|Ser|Gln|Ser|Lys|Ala|Arg|Asp|Thr|Lys|Val|Leu|Ile|Glu|Asp|
| | |610| | | | |615| | | | |620| | | |
|Thr|Asp|Asp|Glu|Ala|Asn|Thr| | | | | | | | | |
|625| | | |630| | | | | | | | | | | |

```
<210> SEQ ID NO 22
<211> LENGTH: 4154
<212> TYPE: DNA
<213> ORGANISM: Homo sapiens
<220> FEATURE:
<221> NAME/KEY: source
<222> LOCATION: 1..4154
<223> OTHER INFORMATION: /mol_type="unassigned DNA"
      /organism="Homo sapiens"

<400> SEQUENCE: 22
ggaggaagat ggcgggcggg ctgctctgaa gagacctcgg cggcggcgga ggaggagaga      60
agcgcagcgc cgcgccgcgc cggggcccat gtggggagga gtcggagtcg ctgttgccgc     120
cgccgcctgt agctgctgga cccgagtggg agtgaggggg aaacggcagg atgaagttcg     180
ccgagcacct ctccgcgcac atcactcccg agtggaggaa gcaatacatc cagtatgagg     240
ctttcaagga tatgctgtat tcagctcagg accaggcacc ttctgtggaa gttacagatg     300
aggacacagt aaagaggtat tttgccaagt ttgaagagaa gttttttccaa acctgtgaaa     360
aagaacttgc caaaatcaac acattttatt cagagaagct cgcagaggct cagcgcaggt     420
ttgctacact tcagaatgag cttcagtcat cactggatgc acagaaagaa agcactggtg     480
ttactacgct gcgacaacgc agaaagccag tcttccactt gtcccatgag aacgtgtcc      540
aacatagaaa tattaaagac cttaaactgg ccttcagtga gttctacctc agtctaatcc     600
tgctgcagaa ctatcagaat ctgaattta cagggtttcg aaaaatcctg aaaaagcatg     660
acaagatcct ggaaacatct cgtggagcag attggcgagt ggctcacgta gaggtggccc     720
cattttatac atgcaagaaa atcaaccagc ttatctctga aactgaggct gtagtgacca     780
atgaacttga agatggtgac agacaaaagg ctatgaagcg tttacgtgtc ccccctttgg     840
gagctgctca gcctgcacca gcatggacta cttttagagt tggcctattt tgtggaatat     900
tcattgtact gaatattacc cttgtgcttg ccgctgtatt taaacttgaa acagatagaa     960
gtatatggcc cttgataaga atctatcggg gtggctttct tctgattgaa ttccttttc    1020
tactgggcat caacacgtat ggttggagac aggctggagt aaaccatgta ctcatctttg    1080
aacttaatcc gagaagcaat ttgtctcatc aacatctctt tgagattgct ggattcctcg    1140
ggatattgtg gtgcctgagc cttctggcat gcttctttgc tccaattagt gtcatcccca    1200
catatgtgta tccacttgcc ctttatggat ttatggtttt cttccttatc aaccccacca    1260
aaactttcta ctataaatcc cggttttggc tgcttaaact gctgtttcga gtatttacag    1320
cccccttcca taaggtaggc tttgctgatt tctggctggc ggatcagctg aacagcctgt    1380
cagtgatact gatggacctg gaatatatga tctgcttcta cagtttggag ctcaaatggg    1440
atgaaagtaa gggcctgttg ccaaataatt cagaagaacg aggtcactcg acactatgg     1500
tgttctttta cctgtggatt gtcttttata tcatcagttc ctgctatacc ctcatctggg    1560
atctcaagat ggactgggt ctcttcgata agaatgctgg agagaacact ttcctccggg    1620
```

-continued

```
aagagattgt ataccccaa aaagcctact actactgtgc cataatagag gatgtgattc    1680
tgcgctttgc ttggactatc caaatctcga ttacctctac aactttgttg cctcattctg    1740
gggacatcat tgctactgtc tttgccccac ttgaggtttt ccggcgattt gtgtggaact    1800
tcttccgcct ggagaatgaa catctgaata actgtggtga attccgtgct gtgcgggaca    1860
tctctgtggc cccctgaac gcagatgatc agactctcct agaacagatg atggaccagg    1920
atgatggggt acgaaaccgc cagaagaatc ggtcatggaa gtacaaccag agcatatccc    1980
tgcgccggcc tcgcctcgct tctcaatcca aggctcgtga cactaaggta ttgatagaag    2040
acacagatga tgaagctaac acttgaattt tctgaagtct agcttaacat ctttggtttt    2100
cctactctac aatcctttcc tcgaccaacg caacctctag taccttttcca gccgaaaaca    2160 ggagaaaaca cataacacat tttccgagct cttccggatc ggatcctatg gactccaaac    2220
aagctcactg tgtttctttt cttttcttct ggtttaattt taattttcta ttttcaaaac    2280
aaatatttac ttcatttgcc aatcagagga tgttttaaga aacaaaacat agtatcttat    2340
ggattgttta caatcacaag gacatagata cctatcagga tgaagaacag gcattgcaag    2400
gaccctctga tgggacggta ctgagatatc tcggcttccg ctcagcccgg ttttgactgg    2460
ttgaaaccgg acattggttt ttaaattttt tgtcagttta tgtggagaat tttttttcttt    2520 ccttcatacc cagcgcaaag gcactggccg cacttgcagg aaaagtgcaa cttaaagcag    2580
taccttcatt catgaagcta cttttttaatt tgatgtaact tttcttattt tgggaagggt    2640
tgctgggtgg gtgggaaata tgatgtattt gttacacata gttttctcat tatttatgaa    2700
acttaaccat acagaatgat ataactcctg tgcaatgaag gtgataacag taaaagaagg    2760
caggggaaac ttacgttgga tgacatttat gagggtcagt cccacatacc tctttcagga    2820
gacaacttgc accagtttga ccttttcttt tctttgtttt tattttaagc caaagtttca    2880
ttgctaactt cttaagttgc tgctgcttta gagtcctgag catatctctc gtaacaagga    2940
atcccacact tcacaccacc ggctgaattt catggaagag gttctgataa tttttttaac    3000
tttttaagga acagatgtgg aatacactgg cccatatttc aaccttaaca gctgaagcta    3060
tgccttatta tgcatccaca tgtatggtcc ctgtagcgtg accttactta gctctgaatc    3120
agaagacaga gctatttcag aggctctgtg tgccctcact agatagtttt tcttctgggt    3180
tcaaccactt tagccagaat tgatcaaat taaaagtctg tcatggggaa actatatttt    3240
tgagcacatg gaacaaatta tacttcctca ttcatattat gttgatacaa aagaccttgg    3300
cagccatttc tcccagcagt tttaaaggat gaacattgga tttcatgcca tcccatagaa    3360
aacctgtttt aaaattttag ggatctttac ttggtcatac atgaaaagta cactgcttag    3420
aaattataga ctattatgat ctgtccacag tgcccattgt cacttctttg tctcatttct    3480 tcccttttgtt ccttagtcat ccaaataagc ctgaaaacca taagagatat tactttattg    3540
aatatggttg gcattaaatt tagcatttca ttatctaaca aaattaatat aaattccagg    3600
acatggtaaa atgtgtttta ataaccccca gacccaaatg aaaatttcaa agtcaatacc    3660
agcagattca tgaaagtaaa tttagtccta taattttcag cttaattata aacaaaggaa    3720
caaataagtg gaagggcagc tattaccatt cgcttagtca aaacattcgg ttactgccct    3780
ttaatacact cctatcatca gcacttccac catgtattac aagtcttgac ccatccctgt    3840
cgtaactcca gtaaaagtta ctgttactag aaaattttta tcaattaact gacaaatagt    3900 ttcttttaa agtagtttct tccatctttta ttctgactag cttccaaaat gtgttccctt    3960
tttgaatcga ggtttttttg ttttgttttg ttttctgaaa aaatcataca actttgtgct    4020
```

-continued

```
tctattgctt ttttgtgttt tgttaagcat gtcccttggc ccaaatggaa gaggaaatgt    4080
ttaattaatg cttttagtt taaataaatt gaatcattta taataaaaaa aaaaaaaaaa    4140
aaaaaaaaaa aaaa                                                      4154
```

<210> SEQ ID NO 23
<211> LENGTH: 492
<212> TYPE: PRT
<213> ORGANISM: Homo sapiens

<400> SEQUENCE: 23

```
Met Glu Pro Ser Ser Lys Lys Leu Thr Gly Arg Leu Met Leu Ala Val
1               5                   10                  15

Gly Gly Ala Val Leu Gly Ser Leu Gln Phe Gly Tyr Asn Thr Gly Val
            20                  25                  30

Ile Asn Ala Pro Gln Lys Val Ile Glu Glu Phe Tyr Asn Gln Thr Trp
        35                  40                  45

Val His Arg Tyr Gly Glu Ser Ile Leu Pro Thr Thr Leu Thr Thr Leu
    50                  55                  60

Trp Ser Leu Ser Val Ala Ile Phe Ser Val Gly Gly Met Ile Gly Ser
65                  70                  75                  80

Phe Ser Val Gly Leu Phe Val Asn Arg Phe Gly Arg Arg Asn Ser Met
                85                  90                  95

Leu Met Met Asn Leu Leu Ala Phe Val Ser Ala Val Leu Met Gly Phe
            100                 105                 110

Ser Lys Leu Gly Lys Ser Phe Glu Met Leu Ile Leu Gly Arg Phe Ile
        115                 120                 125

Ile Gly Val Tyr Cys Gly Leu Thr Thr Gly Phe Val Pro Met Tyr Val
    130                 135                 140

Gly Glu Val Ser Pro Thr Ala Leu Arg Gly Ala Leu Gly Thr Leu His
145                 150                 155                 160

Gln Leu Gly Ile Val Gly Ile Leu Ile Ala Gln Val Phe Gly Leu
                165                 170                 175

Asp Ser Ile Met Gly Asn Lys Asp Leu Trp Pro Leu Leu Leu Ser Ile
            180                 185                 190

Ile Phe Ile Pro Ala Leu Leu Gln Cys Ile Val Leu Pro Phe Cys Pro
        195                 200                 205

Glu Ser Pro Arg Phe Leu Leu Ile Asn Arg Asn Glu Glu Asn Arg Ala
    210                 215                 220

Lys Ser Val Leu Lys Lys Leu Arg Gly Thr Ala Asp Val Thr His Asp
225                 230                 235                 240

Leu Gln Glu Met Lys Glu Glu Ser Arg Gln Met Met Arg Glu Lys Lys
                245                 250                 255

Val Thr Ile Leu Glu Leu Phe Arg Ser Pro Ala Tyr Arg Gln Pro Ile
            260                 265                 270

Leu Ile Ala Val Val Leu Gln Leu Ser Gln Gln Leu Ser Gly Ile Asn
        275                 280                 285

Ala Val Phe Tyr Tyr Ser Thr Ser Ile Phe Glu Lys Ala Gly Val Gln
    290                 295                 300

Gln Pro Val Tyr Ala Thr Ile Gly Ser Gly Ile Val Asn Thr Ala Phe
305                 310                 315                 320

Thr Val Val Ser Leu Phe Val Val Glu Arg Ala Gly Arg Arg Thr Leu
                325                 330                 335

His Leu Ile Gly Leu Ala Gly Met Ala Gly Cys Ala Ile Leu Met Thr
```

```
                340              345                 350
Ile Ala Leu Ala Leu Leu Glu Gln Leu Pro Trp Met Ser Tyr Leu Ser
                355                 360                 365

Ile Val Ala Ile Phe Gly Phe Val Ala Phe Glu Val Gly Pro Gly
            370                 375                 380

Pro Ile Pro Trp Phe Ile Val Ala Glu Leu Phe Ser Gln Gly Pro Arg
385                 390                 395                 400

Pro Ala Ala Ile Ala Val Ala Gly Phe Ser Asn Trp Thr Ser Asn Phe
                405                 410                 415

Ile Val Gly Met Cys Phe Gln Tyr Val Glu Gln Leu Cys Gly Pro Tyr
            420                 425                 430

Val Phe Ile Ile Phe Thr Val Leu Leu Val Leu Phe Phe Ile Phe Thr
                435                 440                 445

Tyr Phe Lys Val Pro Glu Thr Lys Gly Arg Thr Phe Asp Glu Ile Ala
            450                 455                 460

Ser Gly Phe Arg Gln Gly Gly Ala Ser Gln Ser Asp Lys Thr Pro Glu
465                 470                 475                 480

Glu Leu Phe His Pro Leu Gly Ala Asp Ser Gln Val
                485                 490

<210> SEQ ID NO 24
<211> LENGTH: 3687
<212> TYPE: DNA
<213> ORGANISM: Homo sapiens
<220> FEATURE:
<221> NAME/KEY: source
<222> LOCATION: 1..3687
<223> OTHER INFORMATION: /mol_type="unassigned DNA"
      /organism="Homo sapiens"

<400> SEQUENCE: 24
tccaccattt tgctagagaa ggccgcggag gctcagagag gtgcgcacac ttgccctgag      60
tcacacagcg aatgccctcc gcggtcccaa cgcagagaga acgagccgat cggcagcctg     120
agcgaggcag tggttagggg gggccccggc cccggccact cccctcaccc cctccccgca     180
gagcgccgcc caggacaggc tgggcccag gccccgcccc gaggtcctgc ccacacaccc      240
ctgacacacc ggcgtcgcca gccaatggcc ggggtcctat aaacgctacg gtccgcgcgc     300
tctctggcaa gaggcaagag gtagcaacag cgagcgtgcc ggtcgctagt cgcgggtccc     360
cgagtgagca cgccagggag caggagacca aacgacgggg gtcggagtca gagtcgcagt     420
gggagtcccc ggaccggagc acgagcctga gcgggagagc gccgctcgca cgcccgtcgc     480
cacccgcgta cccggcgcag ccagagccac cagcgcagcg ctgccatgga gcccagcagc     540
aagaagctga cgggtcgcct catgctggcc gtgggaggag cagtgcttgg ctccctgcag     600
tttggctaca cactggagt catcaatgcc cccagaagg tgatcgagga gttctacaac      660
cagacatggg tccaccgcta tggggagagc atcctgccca ccacgctcac acgctctgg     720 tccctctcag tggccatctt ttctgttggg ggcatgattg ctccttctc tgtgggcctt     780 ttcgttaacc gctttggccg gcggaattca atgctgatga tgaacctgct ggccttcgtg     840
tccgccgtgc tcatgggctt ctcgaaactg gcaagtcct tgagatgct gatcctgggc      900 cgcttcatca tcggtgtgta ctgcggcctg accacaggct tcgtgcccat gtatgtgggt     960
gaagtgtcac ccacagccct tcgtgggcc ctgggcaccc tgcaccagct gggcatcgtc    1020
gtcggcatcc tcatcgccca ggtgttcggc ctggactcca tcatgggcaa caaggacctg    1080
tggcccctgc tgctgagcat catcttcatc ccggcccctg ctgcagtgcat cgtgctgccc    1140
```

-continued

```
ttctgccccg agagtccccg cttcctgctc atcaaccgca acgaggagaa ccgggccaag    1200
agtgtgctaa agaagctgcg cgggacagct gacgtgaccc atgacctgca ggagatgaag    1260
gaagagagtc ggcagatgat gcgggagaag aaggtcacca tcctggagct gttccgctcc    1320
cccgcctacc gccagcccat cctcatcgct gtggtgctgc agctgtccca gcagctgtct    1380
ggcatcaacg ctgtcttcta ttactccacg agcatcttcg agaaggcggg ggtgcagcag    1440
cctgtgtatg ccaccattgg ctccggtatc gtcaacacgg ccttcactgt cgtgtcgctg    1500
tttgtggtgg agcgagcagg ccggcggacc ctgcacctca taggcctcgc tggcatggcg    1560
ggttgtgcca tactcatgac catcgcgcta gcactgctgg agcagctacc ctggatgtcc    1620
tatctgagca tcgtggccat ctttggcttt gtggccttct ttgaagtggg tcctggcccc    1680
atcccatggt tcatcgtggc tgaactcttc agccagggtc cacgtccagc tgccattgcc    1740
gttgcaggct ctccaactg gacctcaaat tcattgtgg gcatgtgctt ccagtatgtg    1800
gagcaactgt gtggtcccta cgtcttcatc atcttcactg tgctcctggt tctgttcttc    1860
atcttcacct acttcaaagt tcctgagact aaaggccgga ccttcgatga gatcgcttcc    1920
ggcttccggc agggggagc cagccaaagt gacaagacac ccgaggagct gttccatccc    1980
ctgggggctg attcccaagt gtgagtcgcc ccagatcacc agcccggcct gctcccagca    2040
gccctaagga tctctcagga gcacaggcag ctggatgaga cttccaaacc tgacagatgt    2100
cagccgagcc gggcctgggg ctcctttctc cagccagcaa tgatgtccag aagaatattc    2160
aggacttaac ggctccagga ttttaacaaa agcaagactg ttgctcaaat ctattcagac    2220
aagcaacagg ttttataatt ttttttattac tgattttgtt attttttatat cagcctgagt    2280 ctcctgtgcc cacatcccag gcttcaccct gaatggttcc atgcctgagg gtggagacta    2340
agccctgtcg agacacttgc cttcttcacc cagctaatct gtagggctgg acctatgtcc    2400
taaggacaca ctaatcgaac tatgaactac aaagcttcta tcccaggagg tggctatggc    2460
cacccgttct gctggcctgg atctccccac tctagggggtc aggctccatt aggatttgcc    2520
ccttcccatc tcttcctacc caaccactca aattaatctt tctttacctg agaccagttg    2580
ggagcactgg agtgcaggga ggagaggggga agggccagtc tgggctgccg ggttctagtc    2640
tcctttgcac tgagggccac actattacca tgagaagagg gcctgtggga gcctgcaaac    2700
tcactgctca agaagacatg gagactcctg ccctgttgtg tatagatgca agatatttat    2760 atatatttt ggttgtcaat attaaataca gacactaagt tatagtatat ctggacaagc    2820
caacttgtaa atacaccacc tcactcctgt tacttaccta aacagatata aatggctggt    2880
ttttagaaac atggttttga aatgcttgtg gattgagggt aggaggtttg gatgggagtg    2940
agacagaagt aagtggggtt gcaaccactg caacggctta gacttcgact caggatccag    3000
tcccttacac gtacctctca tcagtgtcct cttgctcaaa aatctgtttg atccctgtta    3060
cccagagaat atatacattc tttatcttga cattcaaggc attttctatca catatttgat    3120 agttggtgtt caaaaaaaca ctagttttgt gccagccgtg atgctcaggc ttgaaatgca    3180
ttattttgaa tgtgaagtaa atactgtacc tttattggac aggctcaaag aggttatgtg    3240
cctgaagtcg cacagtgaat aagctaaaac acctgctttt aacaatggta ccatacaacc    3300
actactccat taactccacc cacctcctgc accctccccc acacacacaa aatgaaccac    3360
gttctttgta tgggcccaat gagctgtcaa gctgccctgt gttcatttca tttggaattg    3420 cccctctgg ttcctctgta tactactgct tcatctctaa agacagctca tcctcctcct    3480
```

-continued

```
tcacccctga atttccagag cacttcatct gctccttcat cacaagtcca gttttctgcc    3540
actagtctga atttcatgag aagatgccga tttggttcct gtgggtcctc agcactattc    3600
agtacagtgc ttgatgcaca gcaggcactc agaaaatact ggaggaaata aaacaccaaa    3660
gatatttgtc aaaaaaaaaa aaaaaaa                                       3687
```

```
<210> SEQ ID NO 25
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="Forward primer for XPR1"
      /organism="Artificial Sequence"

<400> SEQUENCE: 25
agagcttggg agacaaagca                                               20

<210> SEQ ID NO 26
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="Reverse primer for XPR1"
      /organism="Artificial Sequence"

<400> SEQUENCE: 26
gtggacacaa cattcgcaac                                               20

<210> SEQ ID NO 27
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="Forward primer for GLUT1"
      /organism="Artificial Sequence"

<400> SEQUENCE: 27
tcactgtgct cctggttctg                                               20

<210> SEQ ID NO 28
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="Reverse primer for GLUT1"
      /organism="Artificial Sequence"

<400> SEQUENCE: 28
cctcgggtgt cttgtcactt                                               20

<210> SEQ ID NO 29
<211> LENGTH: 314
<212> TYPE: PRT
<213> ORGANISM: Artificial Sequence
<220> FEATURE:
<223> OTHER INFORMATION: XMRV.RBD
```

<400> SEQUENCE: 29

Met Glu Ser Pro Ala Phe Ser Lys Pro Leu Lys Asp Lys Ile Asn Pro
1               5                   10                  15

Trp Gly Pro Leu Ile Ile Met Gly Ile Leu Val Arg Ala Gly Ala Ser
            20                  25                  30

Val Gln Arg Asp Ser Pro His Gln Val Phe Asn Val Thr Trp Lys Ile
        35                  40                  45

Thr Asn Leu Met Thr Gly Gln Thr Ala Asn Ala Thr Ser Leu Leu Gly
    50                  55                  60

Thr Met Thr Asp Thr Phe Pro Lys Leu Tyr Phe Asp Leu Cys Asp Leu
65                  70                  75                  80

Val Gly Asp Asn Trp Asp Asp Pro Glu Pro Asp Ile Gly Asp Gly Cys
                85                  90                  95

Arg Ser Pro Gly Gly Arg Lys Arg Thr Arg Leu Tyr Asp Phe Tyr Val
            100                 105                 110

Cys Pro Gly His Thr Val Leu Thr Gly Cys Gly Gly Pro Arg Glu Gly
        115                 120                 125

Tyr Cys Gly Lys Trp Gly Cys Glu Thr Thr Gly Gln Ala Tyr Trp Lys
    130                 135                 140

Pro Ser Ser Ser Trp Asp Leu Ile Ser Leu Lys Arg Gly Asn Thr Pro
145                 150                 155                 160

Lys Gly Gln Gly Pro Cys Phe Asp Ser Ser Val Gly Ser Gly Ser Ile
                165                 170                 175

Gln Gly Ala Thr Pro Gly Gly Arg Cys Asn Pro Leu Val Leu Glu Phe
            180                 185                 190

Thr Asp Ala Gly Lys Arg Ala Ser Trp Asp Ala Pro Lys Thr Trp Gly
        195                 200                 205

Leu Arg Leu Tyr Arg Ser Thr Gly Ala Asp Pro Val Thr Leu Phe Ser
    210                 215                 220

Leu Thr Arg Gln Val Leu Asn Val Gly Pro Arg Val Pro Ile Gly Pro
225                 230                 235                 240

Asn Pro Val Ile Thr Glu Gln Leu Pro Pro Ser Gln Pro Val Gln Ile
                245                 250                 255

Met Leu Pro Arg Pro Pro Arg Pro Pro Ser Gly Ala Ala Ser Met
            260                 265                 270

Val Pro Gly Ala Pro Pro Ser Gln Gln Pro Gly Thr Gly Asp Arg
        275                 280                 285

Leu Leu Asn Leu Val Glu Gly Ala Tyr Gln Ala Leu Asn Leu Thr Ser
    290                 295                 300

Pro Asp Lys Thr Gln Glu Cys Trp Leu Cys
305                 310

<210> SEQ ID NO 30
<211> LENGTH: 310
<212> TYPE: PRT
<213> ORGANISM: Artificial Sequence
<220> FEATURE:
<223> OTHER INFORMATION: PMLV.RBD

<400> SEQUENCE: 30

Met Glu Gly Pro Ala Phe Ser Lys Pro Leu Lys Asp Lys Ile Asn Pro
1               5                   10                  15

Trp Gly Pro Leu Ile Val Leu Gly Ile Leu Ile Arg Ala Gly Val Ser
            20                  25                  30

Val Gln His Asp Ser Pro His Gln Val Phe Asn Val Thr Trp Arg Val
              35                  40                  45

Thr Asn Leu Met Thr Gly Gln Thr Ala Asn Ala Thr Ser Leu Leu Gly
 50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                 85                  90                  95

Gly Arg Lys Arg Ala Arg Thr Phe Asp Phe Tyr Val Cys Pro Gly His
                100                 105                 110

Thr Val Pro Thr Gly Cys Gly Gly Pro Arg Glu Gly Tyr Cys Gly Lys
            115                 120                 125

Trp Gly Cys Glu Thr Thr Gly Gln Ala Tyr Trp Lys Pro Ser Ser Ser
130                 135                 140

Trp Asp Leu Ile Ser Leu Lys Arg Gly Asn Thr Pro Arg Asn Gln Gly
145                 150                 155                 160

Pro Cys Tyr Asp Ser Ser Ala Val Ser Ser Asp Ile Lys Gly Ala Thr
                165                 170                 175

Pro Gly Gly Arg Cys Asn Pro Leu Val Leu Glu Phe Thr Asp Ala Gly
            180                 185                 190

Lys Lys Ala Ser Trp Asp Gly Pro Lys Val Trp Gly Leu Arg Leu Tyr
        195                 200                 205

Arg Ser Thr Gly Thr Asp Pro Val Thr Arg Phe Ser Leu Thr Arg Gln
    210                 215                 220

Val Leu Asn Ile Gly Pro Arg Val Pro Ile Gly Pro Asn Pro Val Ile
225                 230                 235                 240

Thr Asp Gln Leu Pro Pro Ser Arg Pro Val Gln Ile Met Leu Pro Arg
                245                 250                 255

Pro Pro Gln Pro Pro Pro Gly Ala Ala Ser Ile Val Pro Glu Thr
            260                 265                 270

Ala Pro Pro Ser Gln Gln Pro Gly Thr Gly Asp Arg Leu Leu Asn Leu
        275                 280                 285

Val Asp Gly Ala Tyr Gln Ala Leu Asn Leu Thr Ser Pro Asp Lys Thr
    290                 295                 300

Gln Glu Cys Trp Leu Cys
305                 310

<210> SEQ ID NO 31
<211> LENGTH: 301
<212> TYPE: PRT
<213> ORGANISM: Artificial Sequence
<220> FEATURE:
<223> OTHER INFORMATION: PMLV.RBD

<400> SEQUENCE: 31

Met Glu Gly Pro Ala Phe Ser Lys Pro Leu Lys Asp Lys Ile Asn Pro
1 5 10 15

Trp Ala Pro Leu Ile Val Leu Gly Ile Leu Ile Arg Ala Gly Val Ser
20 25 30

Val Pro His Asp Ser Pro His Gln Val Phe Asn Val Thr Trp Arg Val
35 40 45

Thr Asn Leu Met Thr Gly Gln Thr Ala Asn Ala Thr Ser Leu Leu Gly
50 55 60

Thr Met Thr Asp Ala Phe Pro Lys Leu Tyr Phe Asp Leu Cys Asp Leu
65 70 75 80

```
Ile Gly Asp Asp Trp Asp Glu Thr Gly Leu Gly Cys Arg Thr Pro Gly
                85                  90                  95

Gly Arg Lys Arg Ala Arg Thr Phe Asp Phe Tyr Val Cys Pro Gly His
            100                 105                 110

Thr Val Pro Thr Gly Cys Gly Pro Arg Glu Gly Tyr Cys Gly Lys
        115                 120                 125

Trp Gly Cys Glu Thr Thr Gly Gln Ala Tyr Trp Lys Pro Ser Ser Ser
130                 135                 140

Trp Asp Leu Ile Ser Leu Lys Arg Gly Asn Thr Pro Arg Asn Gln Gly
145                 150                 155                 160

Pro Cys Tyr Asp Ser Ser Ala Val Ser Ser Gly Ile Gln Gly Ala Thr
                165                 170                 175

Pro Gly Gly Arg Cys Asn Pro Leu Val Leu Glu Phe Thr Asp Ala Gly
            180                 185                 190

Lys Lys Ala Ser Trp Asp Gly Pro Lys Val Trp Gly Leu Arg Leu Tyr
        195                 200                 205

Arg Ser Thr Gly Thr Asp Pro Val Thr Arg Phe Ser Leu Thr Arg Gln
    210                 215                 220

Val Leu Asn Ile Gly Pro Arg Ile Pro Ile Gly Pro Asn Pro Val Ile
225                 230                 235                 240

Thr Asp Gln Leu Pro Pro Ser Arg Pro Val Gln Ile Met Leu Pro Arg
                245                 250                 255

Pro Pro Gln Pro Ser Pro Thr Gly Ala Ala Ser Ile Gln Pro Gly Thr
            260                 265                 270

Gly Asp Arg Leu Leu Asn Leu Val Asp Gly Ala Tyr Gln Ala Leu Asn
        275                 280                 285

Leu Thr Ser Pro Asp Lys Thr Gln Glu Cys Trp Leu Cys
    290                 295                 300

<210> SEQ ID NO 32
<211> LENGTH: 310
<212> TYPE: PRT
<213> ORGANISM: Artificial Sequence
<220> FEATURE:
<223> OTHER INFORMATION: PMLV.RBD

<400> SEQUENCE: 32

Met Glu Gly Pro Ala Phe Ser Lys Pro Leu Lys Asp Lys Ile Asn Pro
1               5                   10                  15

Trp

```
Trp Asp Leu Ile Ser Leu Lys Arg Gly Asn Thr Pro Gln Asn Gln Gly
145                 150                 155                 160

Pro Cys Tyr Asp Ser Ser Ala Val Ser Ser Asp Ile Lys Gly Ala Thr
            165                 170                 175

Pro Gly Gly Arg Cys Asn Pro Leu Val Leu Glu Phe Thr Asp Ala Gly
        180                 185                 190

Lys Lys Ala Ser Trp Asp Gly Pro Lys Val Trp Gly Leu Arg Leu Tyr
    195                 200                 205

Arg Pro Thr Gly Thr Asp Pro Val Thr Arg Phe Ser Leu Thr Arg Arg
    210                 215                 220

Val Leu Asn Ile Gly Pro Arg Val Pro Ile Gly Pro Asn Pro Val Ile
225                 230                 235                 240

Ala Asp Gln Leu Pro Pro Ser Arg Pro Val Gln Ile Met Leu Pro Arg
                245                 250                 255

Pro Pro Gln Pro Pro Pro Gly Ala Ser Ser Ile Val Pro Glu Thr
            260                 265                 270

Ala Pro Pro Ser Gln Gln Pro Gly Thr Gly Asp Arg Leu Leu Asn Leu
            275                 280                 285

Val Asp Gly Ala Tyr Gln Ala Leu Asn Leu Thr Ser Pro Asp Lys Thr
290                 295                 300

Gln Glu Cys Trp Leu Cys
305             310

<210> SEQ ID NO 33
<211> LENGTH: 182
<212> TYPE: PRT
<213> ORGANISM: Artificial Sequence
<220> FEATURE:
<223> OTHER INFORMATION: HTLV1.RBD

<400> SEQUENCE: 33

Met Gly Lys Phe Leu Ala Thr Leu Ile Leu Phe Phe Gln Phe Cys Pro
1               5                   10                  15

Leu Ile Phe Gly Asp Tyr Ser Pro Ser Cys Cys Thr Leu Thr Ile Gly
            20                  25                  30

Val Ser Ser Tyr His Ser Lys Pro Cys Asn Pro Ala Gln Pro Val Cys
        35                  40                  45

Ser Trp Thr Leu Asp Leu Leu Ala Leu Ser Ala Asp Gln Ala Leu Gln
    50                  55                  60

Pro Pro Cys Pro Asn Leu Val Ser Tyr Ser Ser Tyr His Ala Thr Tyr
65                  70                  75                  80

Ser Leu Tyr Leu Phe Pro His Trp Thr Lys Lys Pro Asn Arg Asn Gly
                85                  90                  95

Gly Gly Tyr Tyr Ser Ala Ser Tyr Ser Asp Pro Cys Ser Leu Lys Cys
            100                 105                 110

Pro Tyr Leu Gly Cys Gln Ser Trp Thr Cys Pro Tyr Thr Gly Ala Val
        115                 120                 125

Ser Ser Pro Tyr Trp Lys Phe Gln His Asp Val Asn Phe Thr Gln Glu
    130                 135                 140

Val Ser Arg Leu Asn Ile Asn Leu His Phe Ser Lys Cys Gly Phe Pro
145                 150                 155                 160

Phe Ser Leu Leu Val Asp Ala Pro Gly Tyr Asp Pro Ile Trp Phe Leu
                165                 170                 175

Asn Thr Glu Pro Ser Gln
            180
```

<210> SEQ ID NO 34
<211> LENGTH: 178
<212> TYPE: PRT
<213> ORGANISM: Artificial Sequence
<220> FEATURE:
<223> OTHER INFORMATION: HTLV4.RBD

<400> SEQUENCE: 34

```
Met Gly Asn Val Leu Phe Leu Thr Leu Leu Ala Thr Leu Gly Ile Pro
1               5                   10                  15

Val Leu Gln Ala Ser Arg Cys Thr Ile Thr Val Gly Ile Ser Ser Tyr
            20                  25                  30

His Ser Ser Pro Cys Ser Pro Ala Gln Pro Leu Cys Thr Trp Ala Leu
        35                  40                  45

Asp Leu Val Ser Ile Thr Lys Asp Gln Leu Leu Tyr Pro Pro Cys Gln
    50                  55                  60

Asn Leu Ile Thr Tyr Ser Asn Tyr His Lys Thr Tyr Ser Leu Tyr Leu
65                  70                  75                  80

Phe Pro His Trp Val Gln Lys Pro Leu Arg Arg Gly Leu Gly Tyr Tyr
                85                  90                  95

Ser Ala Ser Tyr Ser Asp Pro Cys Ser Leu Gln Cys Pro Tyr Leu Gly
            100                 105                 110

Ser Gln Ser Trp Thr Cys Pro Tyr Thr Gly Pro Val Ser Ser Pro Thr
        115                 120                 125

Trp Arg Phe Ser Thr Asp Val Asn Phe Thr Gln Glu Val Ser Arg Val
    130                 135                 140

Ser Leu Lys Leu His Phe Ser Lys Cys Gly Ser Ser Leu Thr Leu Leu
145                 150                 155                 160

Ile Asp Ala Pro Gly Tyr Asp Pro Leu Trp Tyr Leu Thr Ser Glu Pro
                165                 170                 175

Thr Gln
```

<210> SEQ ID NO 35
<211> LENGTH: 233
<212> TYPE: PRT
<213> ORGANISM: Artificial Sequence
<220> FEATURE:
<223> OTHER INFORMATION: XMRV.RBD

<400> SEQUENCE: 35

```
Met Glu Ser Pro Ala Phe Ser Lys Pro Leu Lys Asp Lys Ile Asn Pro
1               5                   10                  15

Trp Gly Pro Leu Ile Ile Met Gly Ile Leu Val Arg Ala Gly Ala Ser
            20                  25                  30

Val Gln Arg Asp Ser Pro His Gln Val Phe Asn Val Thr Trp Lys Ile
        35                  40                  45

Thr Asn Leu Met Thr Gly Gln Thr Ala Asn Ala Thr Ser Leu Leu Gly
    50                  55                  60

Thr Met Thr Asp Thr Phe Pro Lys Leu Tyr Phe Asp Leu Cys Asp Leu
65                  70                  75                  80

Val Gly Asp Asn Trp Asp Asp Pro Glu Pro Asp Ile Gly Asp Gly Cys
                85                  90                  95

Arg Ser Pro Gly Gly Arg Lys Arg Thr Arg Leu Tyr Asp Phe Tyr Val
            100                 105                 110

Cys Pro Gly His Thr Val Leu Thr Gly Cys Gly Gly Pro Arg Glu Gly
        115                 120                 125
```

```
Tyr Cys Gly Lys Trp Gly Cys Glu Thr Thr Gly Gln Ala Tyr Trp Lys
        130                 135                 140

Pro Ser Ser Ser Trp Asp Leu Ile Ser Leu Lys Arg Gly Asn Thr Pro
145                 150                 155                 160

Lys Gly Gln Gly Pro Cys Phe Asp Ser Val Gly Ser Gly Ser Ile
                165                 170                 175

Gln Gly Ala Thr Pro Gly Gly Arg Cys Asn Pro Leu Val Leu Glu Phe
            180                 185                 190

Thr Asp Ala Gly Lys Arg Ala Ser Trp Asp Ala Pro Lys Thr Trp Gly
                195                 200                 205

Leu Arg Leu Tyr Arg Ser Thr Gly Ala Asp Pro Val Thr Leu Phe Ser
210                 215                 220

Leu Thr Arg Gln Val Leu Asn Val Gly
225                 230

<210> SEQ ID NO 36
<211> LENGTH: 229
<212> TYPE: PRT
<213> ORGANISM: Artificial Sequence
<220> FEATURE:
<223> OTHER INFORMATION: PMLV.RBD

<400> SEQUENCE: 36

Met Glu Gly Pro Ala Phe Ser Lys Pro Leu Lys Asp Lys Ile Asn

```
<212> TYPE: PRT
<213> ORGANISM: Artificial Sequence
<220> FEATURE:
<223> OTHER INFORMATION: PMLV.RB

```
Gly Arg Lys Arg Ala Arg Thr Phe Asp Phe Tyr Val Cys Pro Gly His
                100                 105                 110

Thr Val Pro Thr Gly Cys Gly Pro Arg Glu Gly Tyr Cys Gly Lys
            115                 120                 125

Trp Gly Cys Glu Thr Thr Gly Gln Ala Tyr Trp Lys Pro Ser Ser Ser
130                 135                 140

Trp Asp Leu Ile Ser Leu Lys Arg Gly Asn Thr Pro Gln Asn Gln Gly
145                 150                 155                 160

Pro Cys Tyr Asp Ser Ser Ala Val Ser Ser Asp Ile Lys Gly Ala Thr
                165                 170                 175

Pro Gly Gly Arg Cys Asn Pro Leu Val Leu Glu Phe Thr Asp Ala Gly
            180                 185                 190

Lys Lys Ala Ser Trp Asp Gly Pro Lys Val Trp Gly Leu Arg Leu Tyr
        195                 200                 205

Arg Pro Thr Gly Thr Asp Pro Val Thr Arg Phe Ser Leu Thr Arg Arg
210                 215                 220

Val Leu Asn Ile Gly
225

<210> SEQ ID NO 39
<211> LENGTH: 316
<212> TYPE: PRT
<213> ORGANISM: Artificial Sequence
<220> FEATURE:
<223> OTHER INFORMATION: Xeno.RBD

<400> SEQUENCE: 39

Met Leu Val Met Glu Gly Ser Ala Phe Ser Lys Pro Leu Lys Asp Lys
1               5                   10                  15

Ile Asn Pro Trp Gly Pro Leu Ile Val Met Gly Ile Leu Val Arg Ala
            20                  25                  30

Gly

```
Phe Ser Leu Thr Arg Gln Val Leu Asn Val Gly Pro Arg Val Pro Ile
225                 230                 235                 240

Gly Pro Asn Pro Val Ile Thr Asp Gln Leu Pro Pro Ser Gln Pro Val
                245                 250                 255

Gln Ile Met Leu Pro Arg Pro Pro His Pro Pro Ser Gly Thr Val
        260                 265                 270

Ser Met Val Pro Gly Ala Pro Pro Ser Gln Gln Pro Gly Thr Gly
            275                 280                 285

Asp Arg Leu Leu Asn Leu Val Glu Gly Ala Tyr Gln Ala Leu Asn Leu
        290                 295                 300

Thr Ser Pro Asp Lys Thr Gln Glu Cys Trp Leu Cys
305                 310                 315

<210> SEQ ID NO 40
<211> LENGTH: 296
<212> TYPE: PRT
<213> ORGANISM: Artificial Sequence
<220> FEATURE:
<223> OTHER INFORMATION: Xeno.RBD

<400> SEQUENCE: 40

Met Leu Val Met Glu Gly Ser Ala Phe Ser Lys Pro Leu Lys Asp Lys
1               5                   10                  15

Ile Asn Pro Trp Gly Pro Leu Ile Val Met Gly Ile Leu Val Arg Ala
            20                  25                  30

Gly Ala Ser Val Gln Arg Asp Ser Pro His Gln Ile Phe Asn Val Thr
        35                  40                  45

Trp Arg Val Thr Asn Leu Met Thr Gly Gln Thr Ala Asn Ala Thr Ser
50                  55                  60

Leu Leu Gly Thr Met Thr Asp Thr Phe Pro Lys Leu Tyr Phe Asp Leu
65                  70                  75                  80

Cys Asp Leu Val Gly Asp Tyr Trp Asp Pro Glu Pro Asp Ile Gly
                85                  90                  95

Asp Gly Cys Arg Thr Pro Gly Gly Arg Arg Arg Thr Arg Leu Tyr Asp
            100                 105                 110

Phe Tyr Val Cys Pro Gly His Thr Val Pro Ile Gly Cys Gly Gly Pro
        115                 120                 125

Gly Glu Gly Tyr Cys Gly Lys Trp Gly Cys Glu Thr Thr Gly Gln Ala
    130                 135                 140

Tyr Trp Lys Pro Ser Ser Ser Trp Asp Leu Ile Ser Leu Lys Arg Gly
145                 150                 155                 160

Asn Thr Pro Lys Asp Gln Gly Pro Cys Tyr Asp Ser Ser Val Ser Ser
                165                 170                 175

Gly Val Gln Gly Ala Thr Pro Gly Gly Arg Cys Asn Pro Leu Val Leu
            180                 185                 190

Glu Phe Thr Asp Ala Gly Arg Lys Ala Ser Trp Asp Ala Pro Lys Val
        195                 200                 205

Trp Gly Leu Arg Leu Tyr Arg Ser Thr Gly Ala Asp Pro Val Thr Arg
    210                 215                 220

Phe Ser Leu Thr Arg Gln Val Leu Asn Val Gly Pro Arg Val Pro Ile
225                 230                 235                 240

Gly Pro Asn Pro Val Ile Thr Asp Gln Leu Pro Pro Ser Gln Pro Val
                245                 250                 255

Gln Ile Met Leu Pro Arg Pro Pro His Pro Pro Ser Gly Thr Val
        260                 265                 270
```

```
Ser Met Val Pro Gly Ala Pro Pro Pro Ser Gln Gln Pro Gly Thr Gly
        275                 280                 285

Asp Arg Leu Leu Asn Leu Val Gln
    290                 295

<210> SEQ ID NO 41
<211> LENGTH: 879
<212> TYPE: DNA
<213> ORGANISM: Artificial Sequence
<220> FEATURE:
<221> NAME/KEY: source
<222> LOCATION: 1..879
<223> OTHER INFORMATION: /mol_type="unassigned DNA"
      /note="Xeno.RBD"
      /organism="Artificial Sequence"

<400> SEQUENCE: 41
atggaaggtt cagcgttctc aaaacccctt aaagataaga ttaacccgtg ggccccccta     60
atagttatgg ggatcttggt gagggcagga gcctcggtac aacgtgacag ccctcaccag    120
atcttcaatg ttacttggag agttaccaac ctaatgacag gacaaacagc taacgccacc    180
tccctcctgg ggacgatgac agacaccttc cctaaactat attttgacct gtgtgattta    240
gtaggagact actgggatga cccagaaccc gatattgggg atggttgccg cactcccggg    300
ggaagaagaa ggacaagact gtatgacttc tatgtttgcc ccggtcatac tgtaccaata    360
gggtgtggag ggccgggaga gggctactgt ggcaaatggg gatgtgagac cactggacag    420
gcatactgga agccatcatc atcatgggac ctaatttccc ttaagcgagg aaacactcct    480
aaggatcagg gcccctgtta tgattcctcg gtctccagtg gcgtccaggg tgccacaccg    540
gggggtcgat gcaacccccct ggtcttagaa ttcactgacg cgggtagaaa ggccagctgg    600 gatgcccccca aagtttgggg actaagactc tatcgatcca caggggccga cccggtgacc    660
cggttctctt tgacccgcca ggtcctcaat gtaggacccc gcgtccccat tgggcctaat    720
cccgtgatca ctgaccagct acccccatcc caacccgtgc agatcatgct ccccaggcct    780
cctcatcctc ctccttcagg cacggtctct atggtacctg ggctcccccc gccttctcaa    840
caacctggga cgggagacag gctgctaaat ctggtagaa                           879

<210> SEQ ID NO 42
<211> LENGTH: 735
<212> TYPE: PRT
<213> ORGANISM: Artificial Sequence
<220> FEATURE:
<223> OTHER INFORMATION: HTLV4.RBD

<400> SEQUENCE: 42

Met Gly Cys Leu Gly Asn Gln Leu Leu Ile Ala Ile Leu Leu Leu Ser
1               5                   10                  15

Val Tyr Gly Ile Tyr Cys Thr Gln Tyr Val Thr Val Phe Tyr Gly Val
            20                  25                  30

Pro Ala Trp Arg Asn Ala Thr Ile Pro Leu Phe Cys Ala Thr Lys Asn
        35                  40                  45

Arg Asp Thr Trp Gly Thr Thr Gln Cys Leu Pro Asp Asn Gly Asp Tyr
    50                  55                  60

Ser Glu Leu Ala Leu Asn Val Thr Glu Ser Phe Asp Ala Trp Glu Asn
65                  70                  75                  80

Thr Val Thr Glu Gln Ala Ile Glu Asp Val Trp Gln Leu Phe Glu Thr
                85                  90                  95
```

```
Ser Ile Lys Pro Cys Val Lys Leu Ser Pro Leu Cys Ile Thr Met Arg
            100                 105                 110

Cys Asn Lys Ser Glu Thr Asp Arg Trp Gly Leu Thr Lys Ser Ser Thr
            115                 120                 125

Thr Ile Thr Thr Ala Ala Pro Thr Ser Ala Pro Val Ser Glu Lys Ile
            130                 135                 140

Asp Met Val Asn Glu Thr Ser Ser Cys Ile Ala Gln Asn Asn Cys Thr
145                 150                 155                 160

Gly Leu Glu Gln Glu Gln Met Ile Ser Cys Lys Phe Thr Met Thr Gly
                    165                 170                 175

Leu Lys Arg Asp Lys Thr Lys Glu Tyr Asn Glu Thr Trp Tyr Ser Thr
            180                 185                 190

Asp Leu Val Cys Glu Gln Gly Asn Ser Thr Asp Asn Glu Ser Arg Cys
            195                 200                 205

Tyr Ile Asn His Cys Asn Thr Ser Val Ile Gln Glu Ser Cys Asp Lys
            210                 215                 220

His Tyr Trp Asp Thr Ile Arg Phe Arg Tyr Cys Ala Pro Pro Gly Tyr
225                 230                 235                 240

Ala Leu Leu Arg Cys Asn Asp Thr Asn Tyr Ser Gly Phe Met Pro Lys
                    245                 250                 255

Cys Ser Lys Val Val Val Ser Ser Cys Thr Arg Met Met Glu Thr Gln
            260                 265                 270

Thr Ser Thr Trp Phe Gly Phe Asn Gly Thr Arg Ala Glu Asn Arg Thr
            275                 280                 285

Tyr Ile Tyr Trp His Gly Arg Asp Asn Arg Thr Ile Ile Ser Leu Asn
            290                 295                 300

Lys Tyr Tyr Asn Leu Thr Met Lys Cys Arg Arg Pro Gly Asn Lys Thr
305                 310                 315                 320

Val Leu Pro Val Thr Ile Met Ser Gly Leu Val Phe His Ser Gln Pro
                    325                 330                 335

Ile Asn Asp Arg Pro Lys Gln Ala Trp Cys Trp Phe Gly Gly Lys Trp
            340                 345                 350

Lys Asp Ala Ile Lys Glu Val Lys Gln Thr Ile Val Lys His Pro Arg
            355                 360                 365

Tyr Thr Gly Thr Asn Asn Thr Asp Lys Ile Asn Leu Thr Ala Pro Gly
            370                 375                 380

Gly Gly Asp Pro Glu Val Thr Phe Met Trp Thr Asn Cys Arg Gly Glu
385                 390                 395                 400

Phe Leu Tyr Cys Lys Met Asn Trp Phe Leu Asn Trp Val Glu Asp Arg
                    405                 410                 415

Asp Val Thr Thr Gln Arg Pro Lys Glu Arg His Arg Arg Asn Tyr Val
            420                 425                 430

Pro Cys His Ile Arg Gln Val Ile Asn Thr Trp His Lys Val Gly Lys
            435                 440                 445

Asn Val Tyr Leu Pro Pro Arg Glu Gly Asp Leu Thr Cys Asn Ser Thr
            450                 455                 460

Val Thr Ser Leu Ile Ala Asn Ile Asp Trp Thr Asp Gly Asn Gln Thr
465                 470                 475                 480

Asn Ile Thr Met Ser Ala Glu Val Ala Glu Leu Tyr Arg Leu Glu Leu
                    485                 490                 495

Gly Asp Tyr Lys Leu Val Glu Ile Thr Pro Ile Gly Leu Ala Pro Thr
            500                 505                 510

Asp Val Lys Arg Tyr Thr Thr Gly Gly Thr Ser Arg Asn Lys Arg Gly
```

-continued

```
        515                 520                 525

Val Phe Val Leu Gly Phe Leu Gly Phe Leu Ala Thr Ala Gly Ser Ala
    530                 535                 540

Met Gly Ala Ala Ser Leu Thr Leu Thr Ala Gln Ser Arg Thr Leu Leu
545                 550                 555                 560

Ala Gly Ile Val Gln Gln Gln Gln Gln Leu Leu Asp Val Val Lys Arg
                565                 570                 575

Gln Gln Glu Leu Leu Arg Leu Thr Val Trp Gly Thr Lys Asn Leu Gln
            580                 585                 590

Thr Arg Val Thr Ala Ile Glu Lys Tyr Leu Lys Asp Gln Ala Gln Leu
        595                 600                 605

Asn Thr Trp Gly Cys Ala Phe Arg Gln Val Cys His Thr Thr Val Pro
    610                 615                 620

Trp Pro Asn Ala Ser Leu Thr Pro Asp Trp Asn Asn Asp Thr Trp Gln
625                 630                 635                 640

Glu Trp Glu Arg Lys Val Asp Phe Leu Glu Glu Asn Ile Thr Ala Leu
                645                 650                 655

Leu Glu Glu Ala Gln Ile Gln Gln Glu Lys Asn Met Tyr Glu Leu Gln
            660                 665                 670

Lys Leu Asn Ser Trp Asp Val Phe Gly Asn Trp Phe Asp Leu Ala Ser
        675                 680                 685

Trp Ile Lys Tyr Ile Gln Tyr Gly Ile Tyr Val Val Val Gly Val Ile
    690                 695                 700

Leu Leu Arg Ile Val Ile Tyr Ile Val Gln Met Leu Ala Lys Leu Arg
705                 710                 715                 720

Gln Gly Tyr Arg Pro Val Phe Ser Ser Pro Pro Ser Tyr Phe Gln
                725                 730                 735

<210> SEQ ID NO 43
<211> LENGTH: 493
<212> TYPE: PRT
<213> ORGANISM: Artificial Sequence
<220> FEATURE:
<223> OTHER INFORMATION: HTLV3.RBD

<400> SEQUENCE: 43

Met Gly Lys Ser Gly Leu Tyr Phe Ser Leu Ile Cys Phe Tyr Thr Leu
1               5                   10                  15

Phe Pro Ser Ser Phe Gly Asn Pro Ser Arg Cys Thr Leu Phe Ile Gly
            20                  25                  30

Ala Ser Ser Tyr His Ser Asp Pro Cys Gly Ser Asn His Pro Arg Cys
        35                  40                  45

Thr Trp Arg Leu Asp Leu Phe Ser Leu Thr Lys Asp Gln Ser Leu Ser
    50                  55                  60

Pro Pro Cys Pro Gly Leu Val Thr Tyr Ser Gln Tyr His Lys Pro Tyr
65                  70                  75                  80

Ser Leu Tyr Val Phe Pro His Trp Ile Ala Lys Pro Asp Arg Arg Gly
                85                  90                  95

Leu Gly Tyr Tyr Ser Ala Ser Tyr Ser Asp Pro Cys Ala Ile Gln Cys
            100                 105                 110

Pro Tyr Leu Gly Cys Gln Ser Trp Thr Cys Pro Tyr Thr Gly Pro Val
        115                 120                 125

Ser Asn Pro His Trp Lys Tyr Thr Ser Asp Leu Asn Phe Thr Gln Glu
    130                 135                 140

Val Ser Ser Ile Ser Leu His Leu His Phe Ser Lys Cys Gly Ser Ser
```

```
            145                 150                 155                 160
        Phe Ser Phe Leu Leu Asp Ala Pro Gly Tyr Asp Pro Val Trp Leu Leu
                        165                 170                 175

Ser Ser Gln Ala Thr Gln Ile Pro Thr Pro Ala Pro Leu Ile Gln
                    180                 185                 190

Asp Ser Asp Leu Gln His Ile Leu Glu Pro Ser Ile Pro Trp Ser Ser
                        195                 200                 205

Lys Ile Leu Asn Leu Ile Leu Leu Ala Leu Lys Ser Thr Asn Tyr Ser
                        210                 215                 220

Cys Met Val Cys Val Asp Arg Ser Ser Leu Ser Ser Trp His Val Leu
        225                 230                 235                 240

Tyr Asp Pro Leu Lys Ala Pro Ser Ser Pro Asp Pro Gln Ala Gln Ser
                        245                 250                 255

Ile Leu Arg Pro Ser Leu Ala Ile Pro Ala Ser Asn Ile Thr Pro Pro
                    260                 265                 270

Phe Pro Trp Thr His Cys Tyr Arg Pro Pro Leu Gln Ala Ile Ser Ser
                        275                 280                 285

Glu Asn Cys Asn Asn Ser Val Ile Leu Pro Pro Phe Ser Leu Ser Pro
                    290                 295                 300

Ile Pro Asp Val Ser Arg Pro Arg Lys Arg Arg Ala Val Pro Ile Ala
        305                 310                 315                 320

Ile Trp Leu Val Ser Ala Leu Ala Ala Gly Thr Gly Ile Ala Gly Gly
                        325                 330                 335

Val Thr Gly Ser Leu Ser Leu Ala Ser Ser Lys Ser Leu Leu Arg Glu
                    340                 345                 350

Val Asp Gln Asp Ile Asp His Leu Thr Arg Ala Ile Val Lys Asn His
                    355                 360                 365

Asp Asn Ile Leu Arg Val Ala Gln Tyr Ala Ala Gln Asn Arg Arg Gly
                    370                 375                 380

Leu Asp Leu Leu Phe Trp Glu Gln Gly Gly Leu Cys Lys Ala Ile Gln
        385                 390                 395                 400

Glu Gln Cys Cys Phe Leu Asn Ile Ser Asn Thr His Val Ser Val Leu
                        405                 410                 415

Gln Glu Arg Pro Pro Leu Glu Lys Arg Val Ile Thr Gly Trp Gly Leu
                    420                 425                 430

Asn Trp Asp Leu Gly Leu Ser Gln Trp Ala Arg Glu Ala Leu Gln Thr
                    435                 440                 445

Gly Ile Thr Leu Leu Ala Leu Phe Leu Leu Ile Val Val Gly Pro
                450                 455                 460

Cys Val Ile Arg Gln Leu Gln Thr Leu Pro Ser Arg Leu Gln His Arg
        465                 470                 475                 480

Ser Gln Pro Tyr Ser Leu Leu Asn Tyr Glu Thr Asn Leu
                        485                 490

<210> SEQ ID NO 44
<211> LENGTH: 1485
<212> TYPE: DNA
<213> ORGANISM: Artificial Sequence
<220> FEATURE:
<221> NAME/KEY: source
<222> LOCATION: 1..1485
<223> OTHER INFORMATION: /mol_type="unassigned DNA"
      /note="HTLV3.RBD"
      /organism="Artificial Sequence"

<400> SEQUENCE: 44
```

```
atgggtaagt ccggtcttta tttcagtctc atttgttttt acacactctt cccttcctct    60
tttggcaatc ccagccgatg caccctgttc ataggagctt cctcctacca ctctgacccc   120
tgtgggtcca accacccacg atgtacctgg agacttgacc tcttttcctt cacaaaggat   180
caaagcctaa gcccccatg tccaggctta gttacttact cacagtacca taaaccctac    240
tccctatatg tatttcctca ttggatagcc aaacctgacc gtcgaggcct aggttactat   300
tctgcttcct actcggaccc ctgcgctata caatgccctt acctaggatg ccagtcatgg   360
acgtgcccct atacaggtcc ggtgtccaac ccacattgga aatacacctc tgatcttaac   420
ttcacccaag aagtatcatc catttcccta cacttgcact tttccaaatg tgggtcctca   480
ttctcctttc tattagatgc gccaggatat gacccagtgt ggctcctctc atcccaggcc   540
acccaaattc cacccacgcc cgcccctctc atacaggact cagatctcca acatatcctg   600
gaaccttcta tcccatggag ttctaaaatc cttaacctta tcctccttgc tttaaagagc   660
actaattatt cttgcatggt ctgtgtcgat cgctccagcc tctcttcatg gcatgttctg   720
tacgacccac tcaaagcccc cagttcaccc gacccccaag cccagtctat cctacggccc   780
tccttagcca ttcccgccag taacatcacc cctccgtttc cttggaccca ctgctatcgc   840
cctcctctac aggccatctc ctcagaaaac tgcaataact ctgtaatact gccccccttc   900
tccctgtccc caattcctga tgtctctaga ccccggaagc gccgagcagt ccccatcgct   960
atatggctgg tatccgccct agcggccggc acgggtatag caggcggagt taccggctcc  1020
ctgtccctgg cgtccagcaa gagtctgttg cgcgaggttg accaggacat agatcaccta  1080
acccgggcaa ttgtaaagaa ccatgacaac atccttcggg ttgctcagta cgcagcccaa  1140
aatcgccgcg gcctagacct gcttttttgg gagcagggag gtctttgtaa ggccatccag  1200
gagcaatgtt gtttccttaa tatcagcaac acccatgtgt cagtccttca ggaaagacct  1260
cctctagaaa aagggtaat taccggctgg gggctcaatt gggaccttgg gctctcccaa  1320
tgggcccgag aggccctcca gacaggtata acactcttgg ccctctttct cctcctcatt  1380
gtcgtagggc cctgtgtcat acgtcagctg cagacccctcc cctcccgcct gcagcaccgc  1440
agccaaccct actcccttct caattatgaa accaacttat aataa                  1485
```

<210> SEQ ID NO 45  
<211> LENGTH: 2208  
<212> TYPE: DNA  
<213> ORGANISM: Artificial Sequence  
<220> FEATURE:  
<221> NAME/KEY: source  
<222> LOCATION: 1..2208  
<223> OTHER INFORMATION: /mol_type="unassigned DNA"  
     /note="HTLV4.RBD"  
     /organism="Artificial Sequence"

<400> SEQUENCE: 45

```
atgggatgtc ttgggaatca gctgcttatc gccatcttgc ttttaagtgt ctatgggatc      60
tattgtactc aatatgtcac agtcttttat ggtgtaccag cttggaggaa tgcgacaatt     120
cccctcttct gtgcaaccaa gaatagggat acttggggaa caactcagtg cctaccagat     180
aatggtgatt attcagaatt ggcccttaat gttacagaaa gctttgatgc ttgggagaat     240
acagtcacag aacaggcaat agaggacgta tggcaactct ttgagacctc aataaagcct     300
tgtgtaaaat tatccccatt atgcattact atgagatgca ataaaagtga gacagataga     360
tggggattga caaaatcatc aacaacaata acaacagcag caccaacatc agcaccagta     420
tcagaaaaaa tagacatggt caatgagact agttcttgta tagctcagaa taattgcaca     480
```

-continued

```
ggcttggaac aagagcaaat gataagctgt aaattcacca tgacagggtt aaaaagagac    540
aagacaaagg agtacaatga aacttggtac tctacagatt tggtttgtga acaagggaat    600
agcactgata atgaaagcag atgctacata aatcactgta acacttctgt tatccaagag    660
tcttgtgaca aacattattg ggatactatt agatttaggt attgtgcacc tccaggttat    720
gctttgctta gatgtaatga cacaaattat tcaggcttta tgcctaaatg ttctaaggtg    780
gtggtctctt catgcacaag gatgatggag acacagactt ctacttggtt tggctttaat    840
ggaactagag cagaaaatag aacttatatt tactggcatg gtagggataa taggactata    900
attagtttaa ataagtatta taatctaaca atgaaatgta gaagaccagg aaataagaca    960
gttttaccag tcaccattat gtctggattg gttttccact cacaaccaat caatgatagg   1020
ccaaagcagg catggtgttg gtttggagga aaatggaagg atgcaataaa agaggtgaaa   1080
cagaccattg tcaaacatcc caggtatact ggaactaaca atactgataa aatcaattta   1140
acggctcctg gaggaggaga tccagaagtt accttcatgt ggacaaattg cagaggagag   1200
ttcctctact gtaaaatgaa ttggtttcta aattgggtag aggataggga tgtaactacc   1260
cagaggccaa aggaacggca tagaaggaat tacgtgccgt gtcatattag acaagtaatc   1320
aacacttggc ataaagtagg caaaaatgtt tatttgcctc caagagaggg agacctcacg   1380
tgtaactcca cagtgaccag tctcatagca aacatagatt ggactgatgg aaaccaaact   1440
aatatcacca tgagtgcaga ggtggcagaa ctgtatcgat tggagttggg agattataaa   1500
ttagtagaga tcactccgat cggcttggcc cccacagatg tgaagaggta cactactggt   1560
ggcacctcaa gaaataaaag aggggtctttt gtgctagggt tcttgggttt tctcgcaacg   1620
gcaggttctg caatgggcgc ggcgtcgttg acgctgaccg ctcagtcccg gactttattg   1680
gctgggatag tgcagcaaca gcaacagctg ttggacgtgg tcaagagaca acaagaattg   1740
ttgcgactga ccgtctgggg aacaaagaac ctccagacta gggtcactgc catcgagaag   1800
tacttaaagg accaggcgca gctgaatact tggggatgtg cgtttagaca agtctgccac   1860
actactgtac catggccaaa tgcaagtcta acaccagact ggaacaatga tacttggcaa   1920
gagtgggagc gaaaggttga cttcttggag gaaaatataa cagccctcct agaagaggca   1980
caaattcaac aagagaagaa catgtatgaa ttacaaaagt taaatagctg ggatgtgttt   2040
ggcaattggt ttgaccttgc ttcttggata aagtatatac aatatggaat ttatgtagtt   2100
gtaggagtaa tactgttaag aatagtgatc tatatagtac aaatgctagc taagttaagg   2160
caggggtata ggccagtgtt ctcttcccca ccctcttatt tccagtag              2208
```